(12) United States Patent
Sue et al.

(10) Patent No.: US 7,491,789 B2
(45) Date of Patent: Feb. 17, 2009

(54) DISULFIDE-CONTAINING PHENOLIC RESIN AS CURING AGENT FOR EPOXY RESIN

(75) Inventors: Haruaki Sue, Hitachi (JP); Takashi Kumaki, Hitachi (JP); Hideyasu Tsuiki, Hitachi (JP); Hiroshi Matsutani, Tsukuba (JP); Toshihiko Takasaki, Tsukuba (JP); Iwao Fukuchi, Hitachi (JP)

(73) Assignee: Hitachi Chemical Company, Ltd, Tokyo (JP)

( * ) Notice: Subject to any disclaimer, the term of this patent is extended or adjusted under 35 U.S.C. 154(b) by 22 days.

(21) Appl. No.: 11/779,181

(22) Filed: Jul. 17, 2007

(65) Prior Publication Data

US 2008/0051550 A1 Feb. 28, 2008

Related U.S. Application Data

(62) Division of application No. 10/514,501, filed as application No. PCT/JP02/10600 on Oct. 11, 2002.

(30) Foreign Application Priority Data

May 13, 2002 (JP) ............... 2002-137594

(51) Int. Cl.
C07C 321/16 (2006.01)
C08G 75/14 (2006.01)
C08L 63/00 (2006.01)

(52) U.S. Cl. .......... 528/212; 525/390; 525/396; 525/481; 525/523; 568/22

(58) Field of Classification Search .......... None
See application file for complete search history.

(56) References Cited

U.S. PATENT DOCUMENTS

| 2,006,043 A | 6/1935 | Dykstra |
| 2,646,415 A | 7/1953 | Patrick et al. |
| 2,716,083 A | 8/1955 | Tallis |
| 3,222,404 A | 12/1965 | van de Brink et al. |
| 3,234,177 A | 2/1966 | van Schooten |
| 3,299,147 A | 1/1967 | O'Shea |
| 4,021,468 A | 5/1977 | Lind |

FOREIGN PATENT DOCUMENTS

| DE | 2346458 C2 | 4/1974 |
| JP | 62-288626 A | 12/1987 |
| JP | 2-55735 A | 2/1990 |
| JP | 6-332350 | 11/1994 |
| JP | 7-245478 | 9/1995 |
| JP | 11-260865 | 9/1999 |
| JP | 2002-316976 A | 10/2002 |
| JP | 2002-322281 A | 11/2002 |
| JP | 2003-327669 A | * 11/2003 |

* cited by examiner

Primary Examiner—Robert Sellers

(57) ABSTRACT

The present invention discloses a sulfur-containing phenolic resin which comprises an organic group represented by the following formula (1):

$$-R^1-S-R^2-S-R^1- \quad (1)$$

wherein $R^1$ represents a hydrocarbon group having 2 to 6 carbon atoms,
$R^2$ represents a hydrocarbon group having 1 to 10 carbon atoms,
between a phenolic carbon and a phenolic carbon, phenol derivatives represented by the following formula (5):

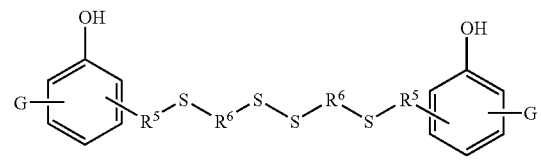

(5)

wherein $R^5$ represents a $C_{2-3}$ alkylene group, $R^6$ represents a $C_{1-10}$ alkylene group, G represents H, a $C_{1-10}$ alkyl group, etc.,
and an epoxy resin composition containing (A) a curing agent of the above-mentioned formula (5) and (B) an epoxy resin as essential components.

1 Claim, 12 Drawing Sheets

DISULFIDE-CONTAINING PHENOLIC RESIN AS CURING AGENT FOR EPOXY RESIN

This is a divisional application of U.S. patent application Ser. No. 10/514,501, filed Nov. 15, 2004 pending, which is a National Phase Application in the United States of International Patent Application No. PCT/JP02/10600 filed Oct. 11, 2002, which claims priority on Japanese Patent Application No. 2002-137594, filed May 13, 2002. The entire disclosures of the above patent applications are hereby incorporated by reference.

TECHNICAL FIELD

The present invention relates to a novel sulfur-containing phenolic resin which can be preferably utilized for a resin for molding materials, an epoxy resin-curing agent, an adhesive, an adhesive film or an anisotropic conductive film, etc., and a process for preparing the same, a novel phenol derivatives and a process for preparing the same, epoxy resin composition, and an adhesive using the same. The phenol derivatives of the present invention show high adhesiveness of a polymer adhesive in a liquid crystal display (LCD) device, a semiconductor mounting materials, and the like. Also, the epoxy resin composition of the present invention is useful for improvement in adhesiveness to a difficulty adherable surface such as gold, etc.

BACKGROUND ART

A phenolic resin has been widely used in the field of electric and electronic appliances such as electronic materials, semiconductor materials, semiconductor packaging materials, color LCD devices, and the like.

Accompanying with a small-sized and light-weight of electric and electronic appliances in recent years, surface mounting type semiconductor package with small and thin-sized such as BGA (Ball Grid Array), CSP (Chip Size Package) and the like is increased. In these semiconductor packages, a surface area covered by gold is markedly increased, and accompalying with this, a surface area occupied by gold plating or gold terminal is also increasing. Therefore, it causes problems in peeling at gold plating or gold terminal, burn out due to the peeling, package crack or the like.

Required characteristics for the phenolic resin to be used in electric and electronic appliances become large such as low modulus of elastics, high heat-resistance, high strength, low hygroscopicity, high adhesiveness, etc. For the purpose of improvement in characteristics, it has been known, for example, to introduce a condensed polycyclic aromatic group such as naphthol (improvement in heat-resistance), or a method of introducing an alkylene chain into a primary chain (low hygroscopicity) and the like.

Also, when a phenolic resin is used for a semiconductor package, the phenolic resin itself has properties of hard and brittle, so that it has been generally carried out to use other materials in combination (for example, an epoxy resin or a plasticizer a plasticizer) to lower modulus of elasticity of the whole resin system whereby the material is made low stress.

A phenolic resin is also one of the materials widely been used as an adhesive for a liquid crystal display device (LCD) for electric and electronic parts or a semi-conductor package. Also, specific phenol derivatives may be sometimes used for heightening various properties of an adhesive.

For example, in a conductive adhesive, in addition to an epoxy resin as a substrate resin, a polyallylphenolic resin is formulated as a curing agent to prepare an adhesive (Japanese Unexamined Patent Publication No. Hei. 6-322350).

In a tape attached with an adhesive for TAB, in addition to a polyimide resin which is a constitutional component for an adhesive, a phenol derivatives in which a sulfur atom or an oxygen atom is introduced between phenol carbon-phenol carbon is added to obtain a tape attached with an adhesive for TAB having high adhesiveness and high insulating property (Japanese Unexamined Patent Publication No. Hei. 11-260865).

Also, in an adhesive for a substrate of a flexible printing circuit, a sulfur-containing phenol derivatives having a specific structure is formulated as an antioxidant for an acrylonitrile-butadiene rubber which is a constitutional component other than a thermosetting resin (Japanese Unexamined Patent Publication No. Hei. 7-245478).

On the other hand, accompanying with further small-sizing and light-weightening of a liquid crystal display device (LCD) or a semiconductor package, more progressed high density packaging techniques have been required. Also, as a surface layer of a material to be adhered such as an anisotropic conductive film (ACF) or a die bond film in recent years, which are objects of an adhesive to be adhered, in addition to copper, a metal material difficulty adhered such as silver, gold, gold/palladium, or silicon nitride, etc. is relatively increasing.

As mentioned above, it has been known that a whole resin system is made not brittle in combination with other plasticizer, but a phenolic resin in which the resin itself is made soft whereby it has a property of not brittle has never been known. An object of the present invention is to develop a novel phenolic resin in which the resin itself is soft, and therefore, it is not brittle (having flexibility).

Also, a surface layer of a material to be adhered such as an anisotropic conductive film (ACF) or a die bond film, which are objects of an adhesive to be adhered, is likely affected by contamination. To the surfaces of such metallic materials, there are some cases that cannot necessarily be satisfied by the conventional adhesives in the points of adhesiveness, stability and the like.

An object of the present invention is to provide a novel phenol derivatives, and another object is to provide an adhesive showing an excellent adhesive force on a surface layer coated with a metal material such as copper, silver, gold, gold/palladium, etc.

DISCLOSURE OF THE INVENTION

In order to accomplish the above-mentioned objects, the present inventors have conceived to synthesize a phenolic resin into which an organic group having a specific structure containing hetero sulfur atom to a main chain structure, and studied variously to complete the present invention.

Also, the present inventors have studied variously on a compound or an adhesive showing an excellent adhesive force on a metal surface coated with copper, silver, gold, gold/palladium, etc., and found that, a phenol derivatives having a thioether structure or a disulfide structure, or an epoxy resin composition to which a phenolic resin having a disulfide structure is added adhesive greatly contribute to improvement in adhesiveness or improvement in adhesiveness to gold to complete the present invention.

That is, the present invention relates to a sulfur-containing phenolic resin having an organic group represented by the following formula (1):

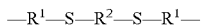  (1)

wherein $R^1$ represents a hydrocarbon group having 2 to 6 carbon atoms, and
$R^2$ represents a hydrocarbon group having 1 to 10 carbon atoms, between the phenolic carbon-phenolic carbon.

A process for preparing the above-mentioned sulfur-containing phenolic resin of the present invention comprises reacting a phenol having an unsaturated hydrocarbon group represented by the following formula (2):

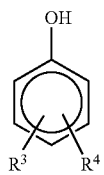  (2)

wherein $R^3$ represents the same hydrocarbon group having 2 to 6 carbon atoms as that of $R^1$ except for having a double bond, $R^4$ represents a methoxy group, a hydroxyl group, a halogen atom or a hydrocarbon group having 1 to 9 carbon atoms, and formaldehyde to obtain dinuclear phenol derivatives represented by the following formula (3):

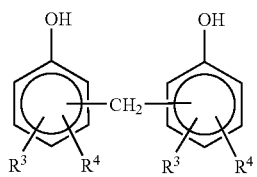  (3)

wherein $R^3$ and $R^4$ have the same meanings as defined above, and then, reacting it with a dithiol compound represented by the formula (4):

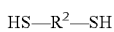  (4)

wherein $R^2$ represents a hydrocarbon group having 1 to 10 carbon atoms.

The resulting sulfur-containing phenolic resin contains, as mentioned above, a soft hydrocarbon group, i.e., a molecular structure of alkyl chains ($R^1$, $R^2$), and two sulfide (—S—) structures, simultaneously, between the phenolic carbon-phenolic carbon (main chain structure of the phenolic resin).

Also, the phenol derivatives of the present invention is characterized in that it has a disulfide structure represented by the following formula (5):

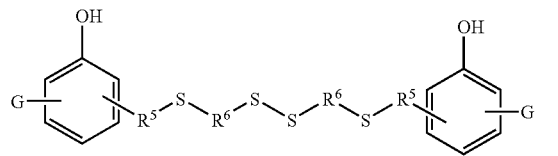  (5)

wherein $R^5$ may be the same or different from each other, and each represent an alkylene group having 2 or 3 carbon atoms, $R^6$ may be the same or different from each other, and each represent an alkylene group having 1 to 10 carbon atoms, and G represents a hydrogen atom, an alkyl group having 1 to 10 carbon atoms, an alkoxyl group having 1 to 10 carbon atoms, a thioalkoxyl group having 1 to 10 carbon atoms, a hydroxyl group, a thiol group, a carboxyl group, a sulfonyl group, a nitro group, an amino group, a cyano group, a phenyl group, a benzyl group or a halogen atom.

Further, the phenol derivatives of the present invention is characterized in that it has a thioether structure represented by the formula (6):

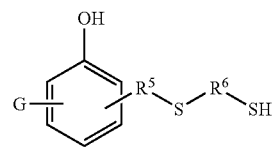  (6)

wherein $R^5$, $R^6$ and G have the same meanings as defined above.

Moreover, a process for preparing the phenol derivatives of the formula (6) according to the present invention comprises heating and reacting a phenol compound represented by the following formula (7) or the following formula (8):

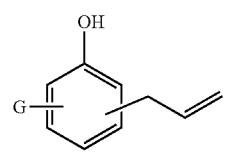  (7)

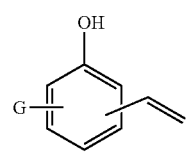  (8)

wherein G has the same meaning as defined above, with a dithol represented by the formula (9):

(9)

wherein $R^6$ has the same meaning as defined above.

Furthermore, the present invention also relates to a process for preparing the phenol derivatives of the above-mentioned formula (5) which comprises subjecting the phenol derivatives of the formula (6) thus obtained to oxidation reaction in a solvent by using hydrogen peroxide.

The epoxy resin composition of the present invention comprises

The present invention further relates to the epoxy resin composition as mentioned above, wherein $R^5$ in the general formula (5) is an alkylene group having 3 carbon atoms, the epoxy resin composition as mentioned above, wherein $R^6$ in the general formula (5) is an alkylene group having 2, 3 or 6 carbon atoms, the epoxy resin composition as mentioned any one of the above, wherein G in the general formula (5) is a hydrogen atom or a methoxy group, the epoxy resin composition as mentioned any one of the above, wherein a content of the disulfide-containing phenolic resin represented by the general formula (5) is 0.1 to 80% by weight based on the whole amount of (A) the curing agent, and further the epoxy resin composition as mentioned any one of the above, wherein it contains (C) a curing accelerator, and an adhesive containing the epoxy resin composition as mentioned any one of the above.

BEST MODE TO CARRY OUT THE INVENTION

Figure 1:
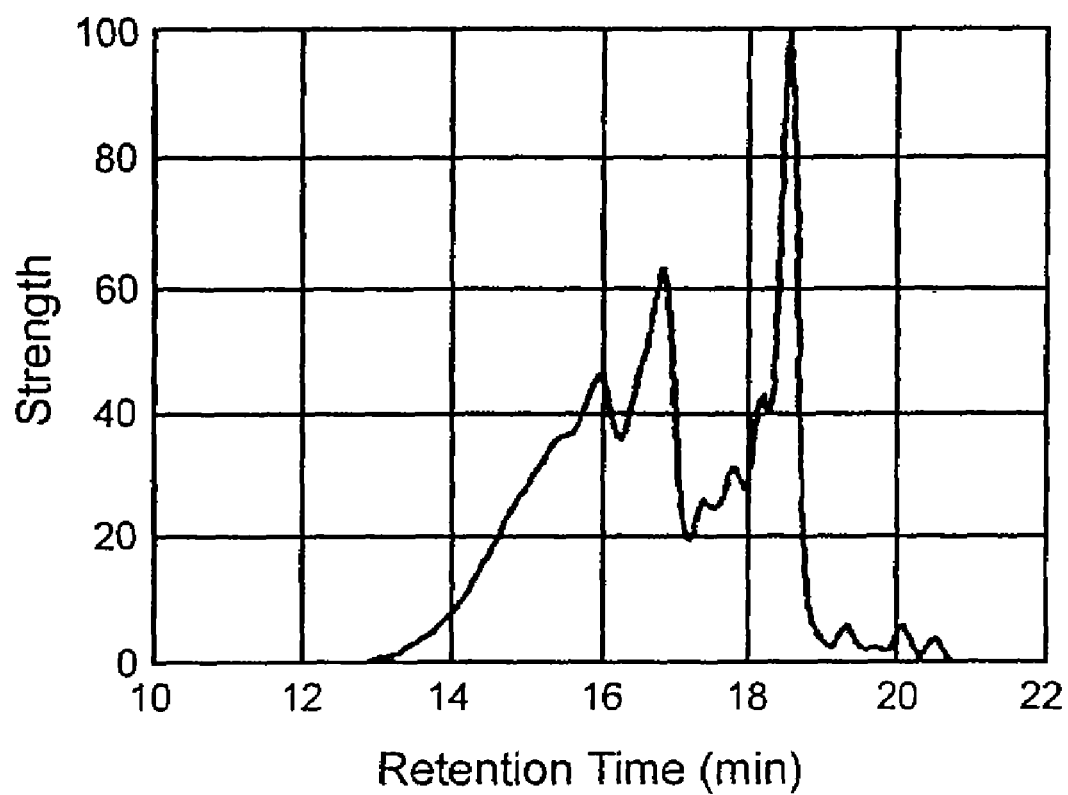
FIG. 1 shows a GPC chart of the resin obtained in Synthetic example 1.

Embodiments of the present invention are explained in more detail.

The sulfur-containing phenolic resin of the present invention has, as described above, an organic group represented by:

(1)

wherein $R^1$ represents a hydrocarbon group having 2 to 6 carbon atoms, and $R^2$ represents a hydrocarbon group having 1 to 10 carbon atoms, between the phenolic carbon-phenolic carbon.

This sulfur-containing phenolic resin can be specifically shown by the following formula (12).

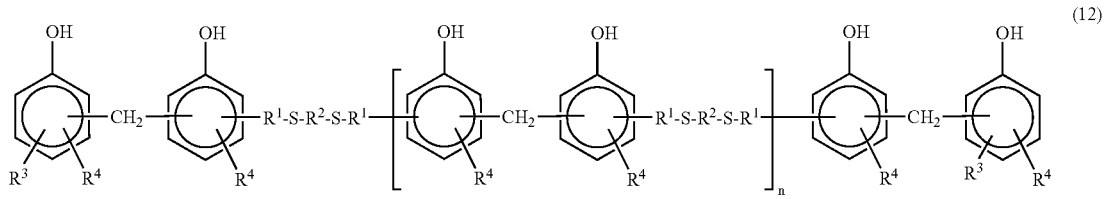

(12)

wherein R¹ and R² have the same meanings as defined above,

R³ represents the same hydrocarbon group having 2 to 6 carbon atoms as that of R¹ except for having a double bond, R⁴ represents a methoxy group, a hydroxyl group, a halogen atom or a hydrocarbon group having 1 to 9 carbon atoms, and n represents a recurring number which may be 0.

The above-mentioned sulfur-containing phenolic resin can be shown, more specifically, by the following formula (13).

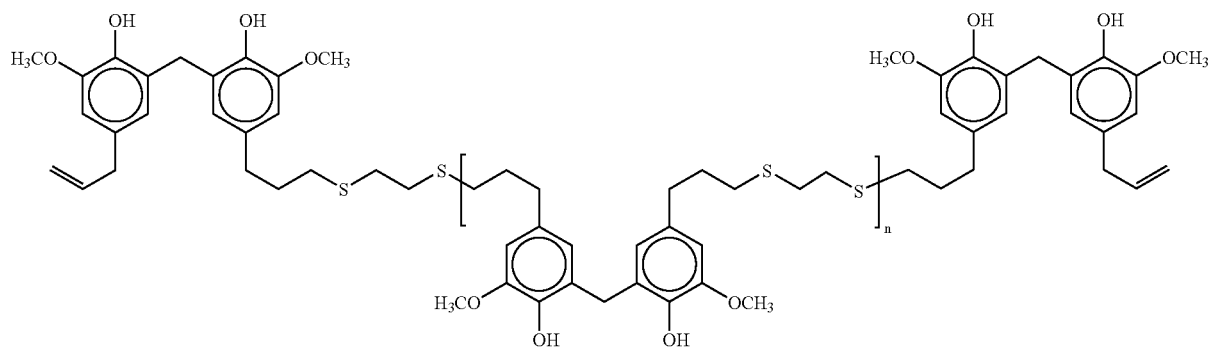

(13)

wherein n represents a recurring number which may be 0.

Next, by referring to the sulfur-containing phenolic resin of the above-mentioned formula (13) as an example, a preparation method thereof is explained.

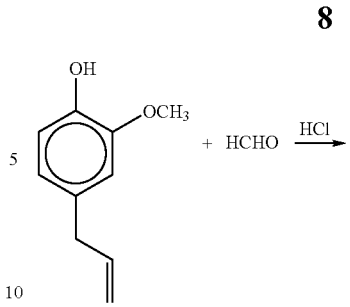

-continued

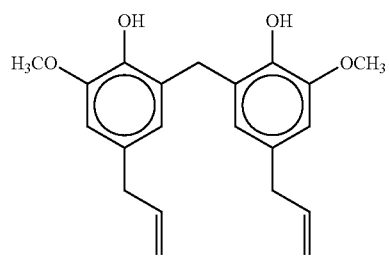

A phenol substituted by an allyl group (or a vinyl group) and formaldehyde are reacted under synthetic conditions of a novolac resin which are general for a phenolic resin synthesis.

When the phenol substituted by an allyl group (or a vinyl group) is one which is an ortho (or para)-substituted material as shown in the following reaction formula, an amount of the formaldehyde to be used based on the phenols is stoichiometrically 0.5 equivalent, and an amount of 0.5 equivalent or more may be used. When 0.5 equivalent or more is used, dinuclear materials can be formed. These reactions are carried out by formulating a phenol substituted by an unsaturated hydrocarbon group, formaldehyde and a catalyst (an acid such as hydrochloric acid, etc.) and reacted at 50 to 100° C. for 1 to 12 hours. Thereafter, the reaction mixture is concentrated at 140 to 200° C. under reduced pressure and unreacted component(s) was removed.

Incidentally, the phenol substituted by an allyl group (or a vinyl group) has no substituent at the ortho position or para position, an amount of the formaldehyde based on the amount of the phenol is made 0.5 equivalent or less than 0.5 equivalent (preferably about 0.3 equivalent). If the amount of the formaldehyde to be used exceeds 0.5 equivalent, in addition to the dinuclear material, a polynuclear product is easily formed. When the formed amount of the polynuclear product is large, a sulfur-containing phenolic resin obtained in the next reaction becomes a branched structure, so that it is crosslinked intermolecularly or intramolecularly to become insoluble or infusible. However, even when it became a branched structure, flexibility or adhesive property would not be impaired.

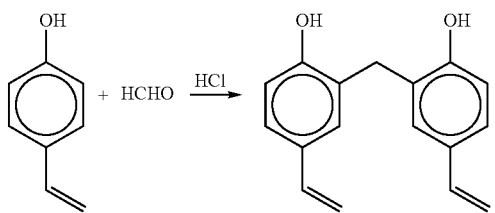

Next, a phenol dinuclear material having an allyl group (or a vinyl group) obtained by the above-mentioned reaction and a dithol are reacted (the following formula is an example of an allyl group) to obtain a sulfur-containing phenolic resin of the formula (13). A reaction of an allyl group and the thiol proceed under heating at 40 to 150° C. without any catalyst, and preferably carried out by using a radical initiator, a cationic initiator or an anionic initiator, and reacted at a temperature of 50 to 150° C. When the temperature is low, a time required for the reaction becomes long, while it is high, thermal polymerization of double bonds easily proceeds. As a radical initiator, there may be mentioned, for example, benzoyl peroxide (BPO), dicumyl peroxide, azobisisobutyronitrile (AIBN) and the like. A time of the reaction may vary depending on the reaction system. It is generally 4 to 24 hours. After the reaction, the mixture is concentrated at 100 to 180° C. under reduced pressure and unreacted material(s) is/are removed.

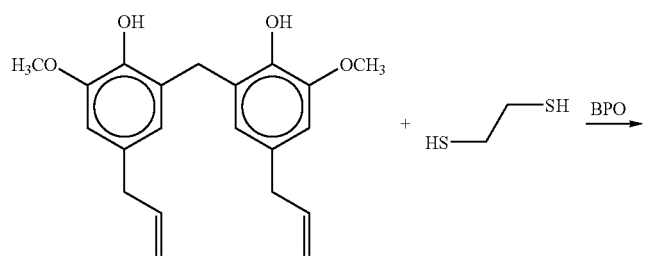

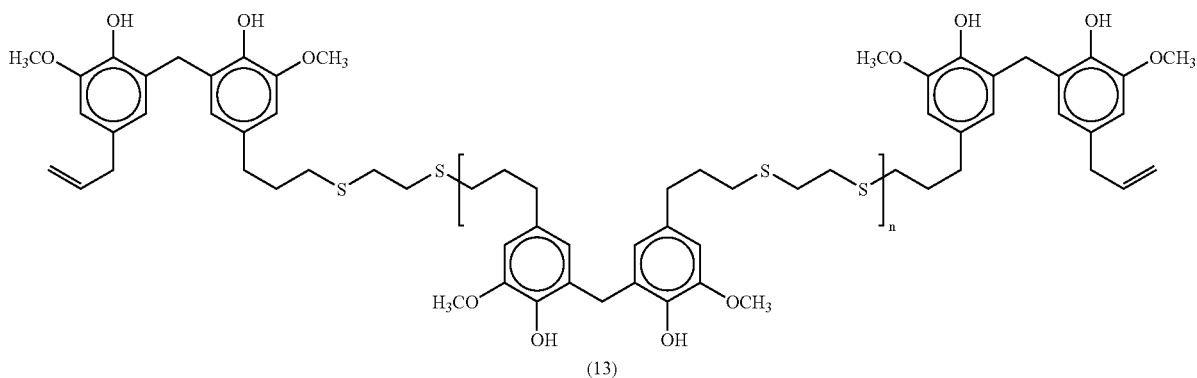

(13)

Incidentally, as the phenol of the above-mentioned formula (2) which is substituted by an unsaturated hydrocarbon group and used as a starting material of the reaction, there may be mentioned, for example, an allylphenol such as 2-allylphenol, 4-allylphenol, 3-allylphenol, 4-allyl-2-methoxyphenol, etc., a vinylphenol such as 2-vinylphenol, 4-vinylphenol, divinylphenol, etc., and butenephenol and the like, and they may be used singly or in combination of two or more.

The phenol derivatives having a disulfide structure of the present invention are phenol derivatives having a disulfide structure represented by the formula (5) as mentioned above.

Here, when $R^5$ is an alkylene group having 3 carbon atoms, the above-mentioned phenol derivatives are shown by the following formula (22).

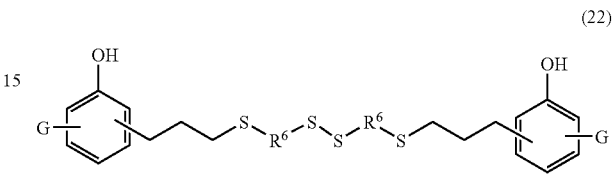

(22)

wherein $R^6$ represents an alkylene group having 1 to 10 carbon atoms, and G represents a hydrogen atom, an alkyl group having 1 to 10 carbon atoms, an alkoxyl group having 1 to 10 carbon atoms, a thioalkoxyl group having 1 to 10 carbon atoms, a hydroxyl group, a thiol group, a carboxyl group, a sulfonyl group, a nitro group, an amino group, a cyano group, a phenyl group, a benzyl group or a halogen atom.

When G is a methoxy group, the above-mentioned phenol derivatives are shown by, for example, the following formula (23), and when G is a hydrogen atom, the above-mentioned phenol derivatives are shown by, for example, the following formula (24).

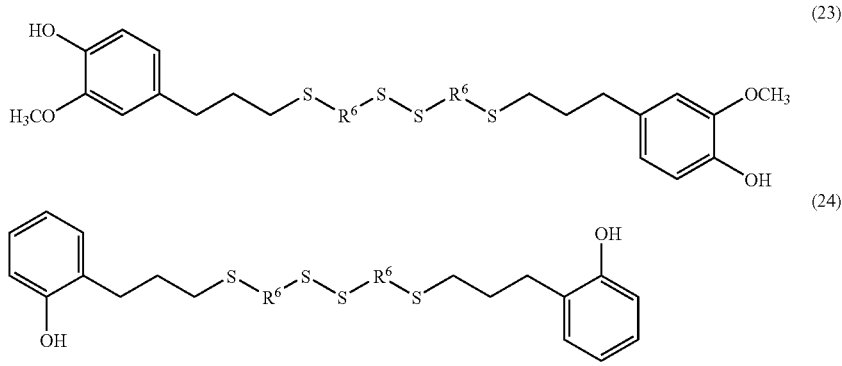

wherein R⁶ has the same meaning as defined above.

The phenol derivatives having a disulfide structure of the present invention are phenol derivatives represented by the formula (6) as mentioned above.

Here, when $R^5$ is an alkylene group having 3 carbon atoms, the above-mentioned phenol derivatives are shown by the following formula (25).

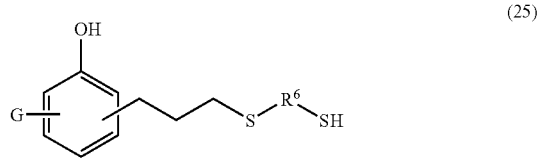

wherein $R^6$ and G have the same meanings as defined above.

When G is a methoxy group, the above-mentioned phenol derivatives are shown by, for example, the following formula (26), and when G is a hydrogen atom, the above-mentioned phenol derivatives are shown by, for example, the following formula (27).

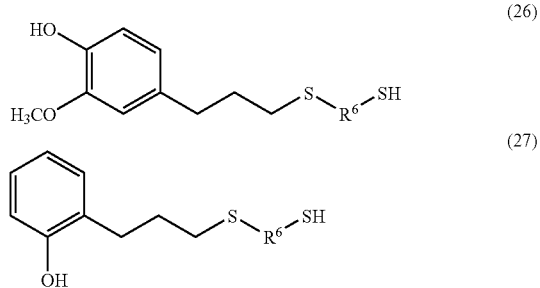

wherein $R^6$ has the same meaning as defined above.

A preparation method of the phenol derivatives having a thioether structure of the formula (6) according to the present invention is firstly explained.

A predetermined amount of the phenol substituted by an allyl group of the formula (7) or the phenol substituted by a vinyl group of the formula (8) is weighed in a reaction vessel, then, a predetermined amount of the dithol of the formula (9) is added thereto. Here, an amount of the phenol of the formula (7) or the phenol of the formula (8) and an amount of the dithol of the formula (9) are basically an equal molar ratio. If one of which is in excess of the other, the excessive amount remain unreacted so that it is not preferred.

Reaction conditions such as a reaction temperature or a reaction time are so selected that the reaction (nucleophilic substitution reaction) sufficiently proceeds. Generally speaking, the reaction temperature is 100° C. to 200° C., and the reaction time is 30 minutes to 7 hours or so.

The reaction is more specifically explained. The reaction is carried out by stirring a mixture in a reaction vessel under reflux and heating. The atmosphere may be an inert atmosphere such as a nitrogen gas, etc., and generally carried out in air. When the reaction conditions are maintained for a predetermined period of time, the phenol derivatives (phenolic monothiol) of the formula (6) can be obtained. The obtained phenol derivatives (phenolic monothiol) may be isolated from the reaction products mixed system and purified, or without isolation and purification, the obtained product may be used as a starting material for the preparation of the phenol derivatives of the formula (5).

Next, the obtained phenol derivatives (phenolic monothiol) are subjected to oxidation reaction in a solvent using hydrogen peroxide to obtain a phenol derivatives of the formula (5). Hydrogen peroxide can be used those commercially available as an aqueous hydrogen peroxide solution (30-35% aqueous solution), and an amount thereof to be used is an equal mol or substantially equal mol to that of the phenol derivatives (phenolic monothiol) used as a substrate.

As the solvent to be used, a solvent which dissolves both of the phenol derivatives of the formula (5) and water (that present in an aqueous hydrogen peroxide solution) may be used and, for example, an alcohol such as methanol, ethanol, etc., or acetone and the like may be used, preferably ethanol.

Reaction conditions such as a reaction temperature or a reaction time are so selected that the oxidation reaction sufficiently proceeds. Generally speaking, the reaction temperature is 50° C. to 70° C., and the reaction time is 1 hour to 3 hours or so.

The reaction is more specifically explained. A suitable amount of the phenol derivatives (phenolic monothiol) is weighed in a reaction vessel, to the derivatives is gradually added dropwise an aqueous hydrogen peroxide solution diluted by ethanol (an aqueous hydrogen peroxide solution diluted by an equal weight of ethanol). An amount to be added dropwise at this time is an equal mol or a substantially equal mol in terms of the hydrogen peroxide based on the amount of the phenol derivatives (phenolic monothiol). Thereafter, the mixture is heated to 50° C. to 70° C. while stirring. Progress of the reaction is confirmed by GPC. After completion of the reaction, the reaction product is extracted with acetone and distilled water, and further concentrated by an evaporator to obtain the phenol derivatives (phenolic disulfide) of the formula (5).

Incidentally, GPC traced the progress of the reaction is carried out by using tetrahydrofuran (THF) as an eluent, and a measurement concentration is made 2.0 g/L. The measurement apparatus was C-R4A manufactured by Shimadzu Corporation, a column was TSK gel G3000HXL+TSK gel G2000HXL manufactured by Tosoh Corporation, an RI monitor was L-3300 manufactured by Hitachi Ltd., and a pump was L-6000 manufactured by Hitachi Ltd.

As (A) a curing agent to be used in the present invention, it is not specifically limited so long as it contains the disulfide-containing phenolic resin represented by the above-mentioned general formula (5), and the disulfide-containing phenolic resin represented by the general formula (5) may be used alone, or one or more other phenolic resins may be used in combination.

$R^5$, $R^6$ and G in the above-mentioned the general formula (5) are each independently selected, and two $R^5$s may be the same or different from each other, two $R^6$s may be the same or different from each other, and two Gs may be the same or different from each other. The disulfide-containing phenolic resin represented by the above-mentioned the general formula (5) may have a symmetric structure, or at least one pair of $R^5$s, $R^6$s, and Gs may have a different asymmetric structure, and a symmetric structure is preferred.

As the disulfide-containing phenolic resin represented by the above-mentioned the general formula (5), there may be mentioned, for example, compounds represented by the following general formulae (II) to (XXXXIII) and the like.

Of the disulfide-containing phenolic resins represented by the above-mentioned the general formula (5), a compound in which $R^5$ in the above-mentioned the general formula (5) is an alkylene group having 3 carbon atoms, a compound in which $R^6$ is an alkylene group having 2, 3 or 6 carbon atoms, a compound in which G is a hydrogen atom or a methoxy group are each preferred, and as such compounds, there may be mentioned, for example, a compound represented by the following general formula (IV), (XVIII) or (XXXII) and the like may be mentioned as a preferably used compound.

These disulfide-containing phenolic resins represented by the above-mentioned the general formula (5) may be used alone or in combination of two or more.

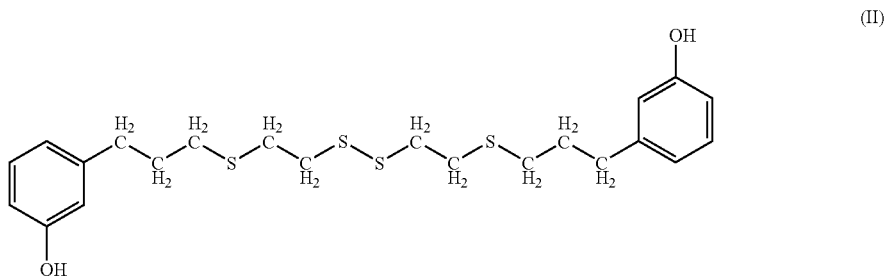

(II)

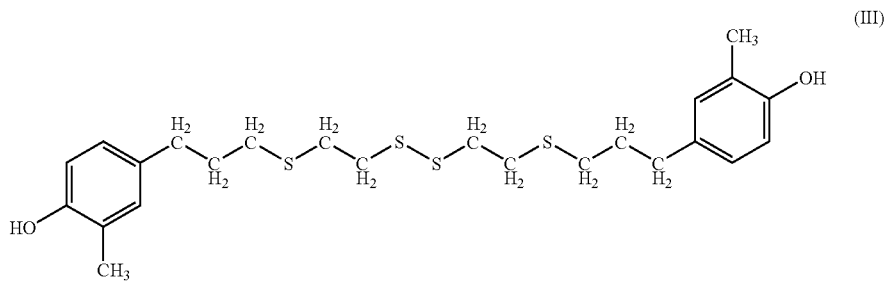

(III)

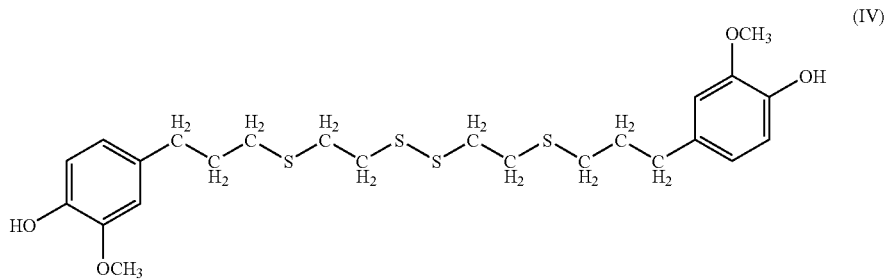

(IV)

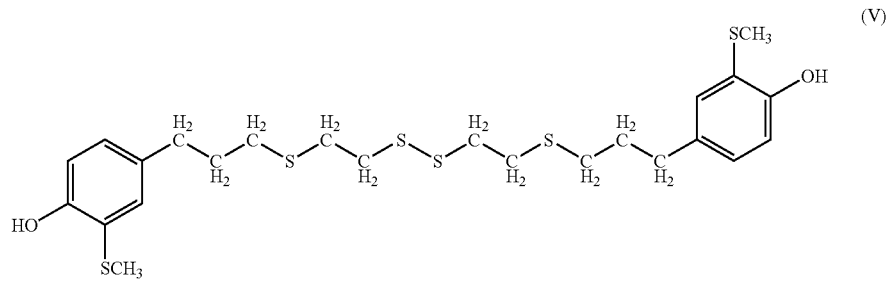
(V)
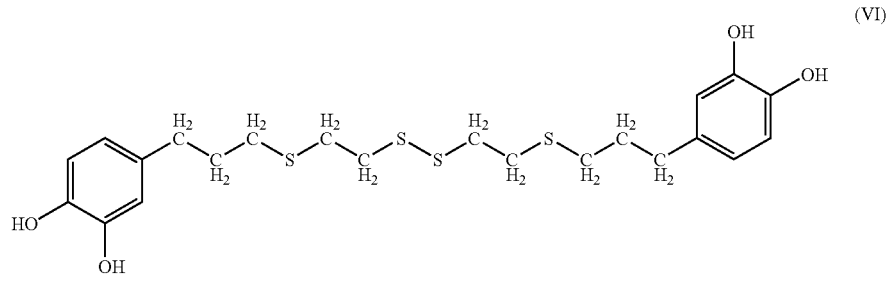
(VI)
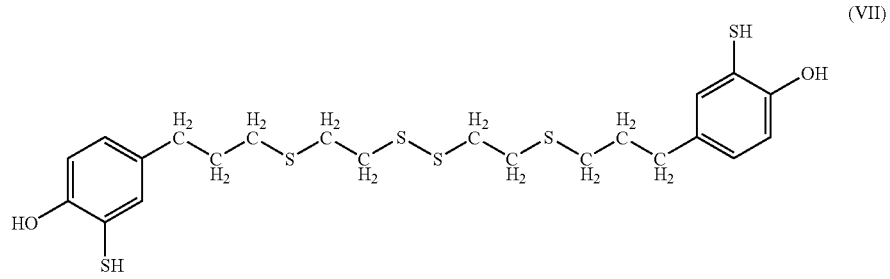
(VII)
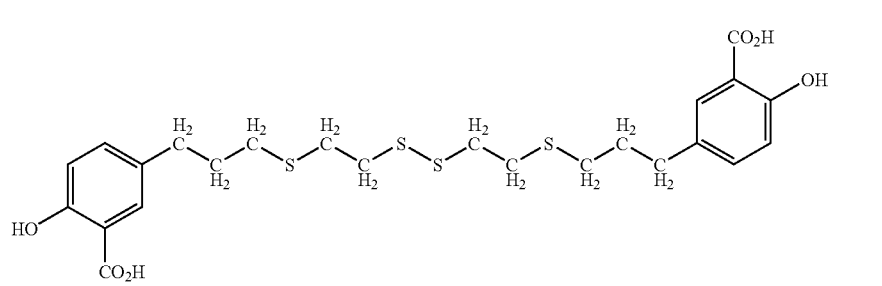
(VIII)
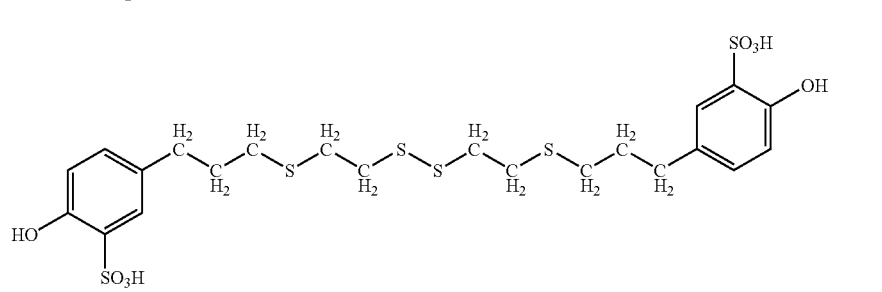
(IX)
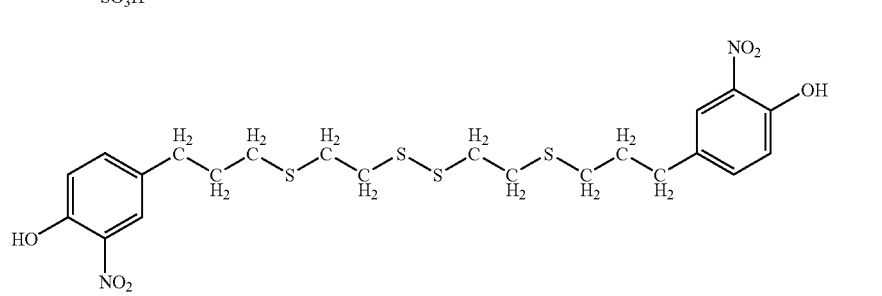
(X)

-continued
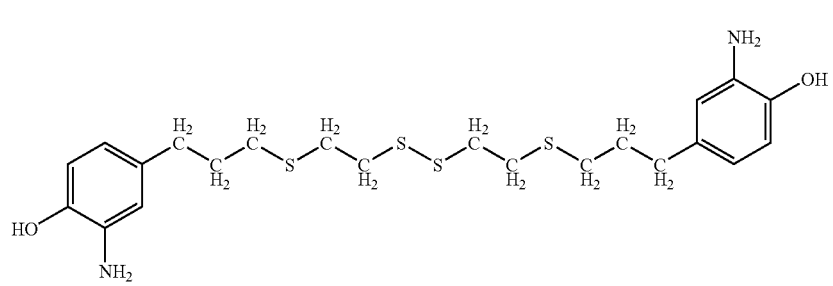
(XI)
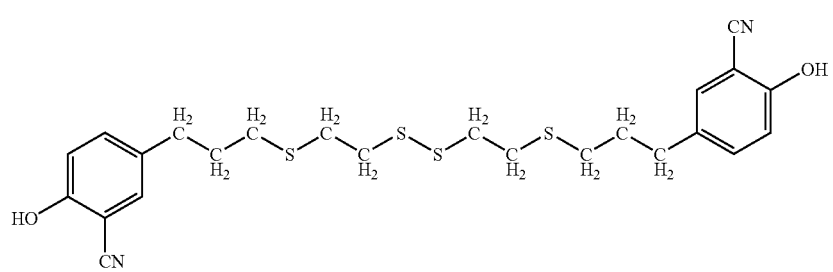
(XIII)
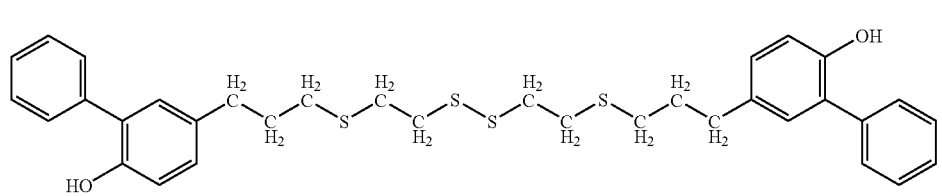
(XIII)
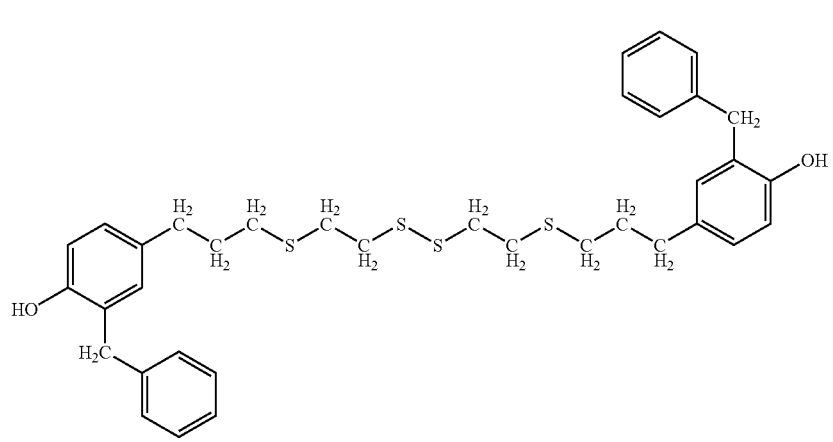
(XIV)
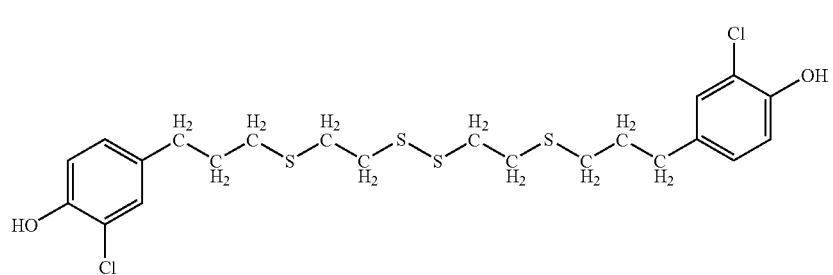
(XV)

XVI
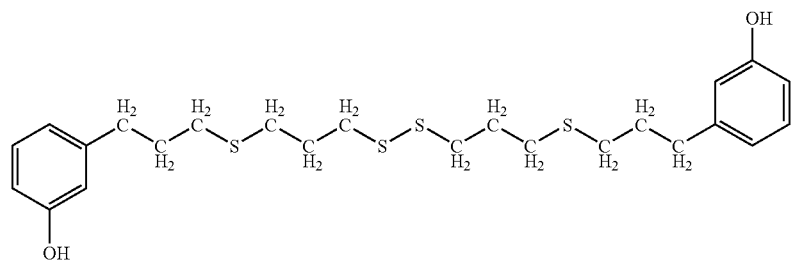
(XVII)
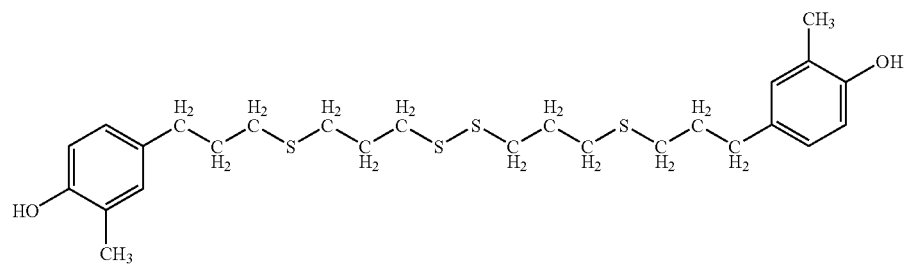
(XVIII)
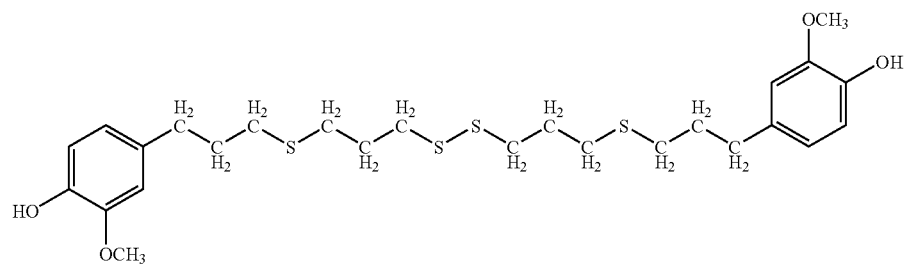
(XIX)
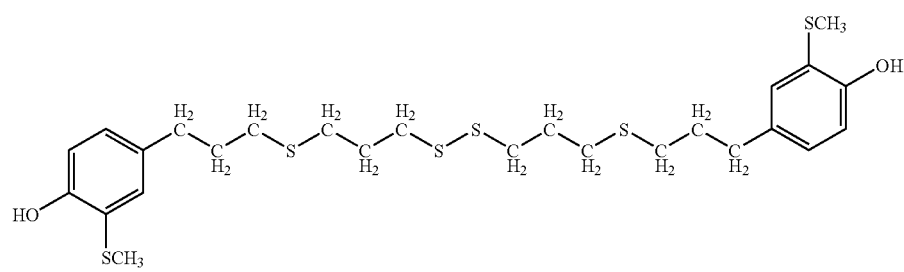
(XX)
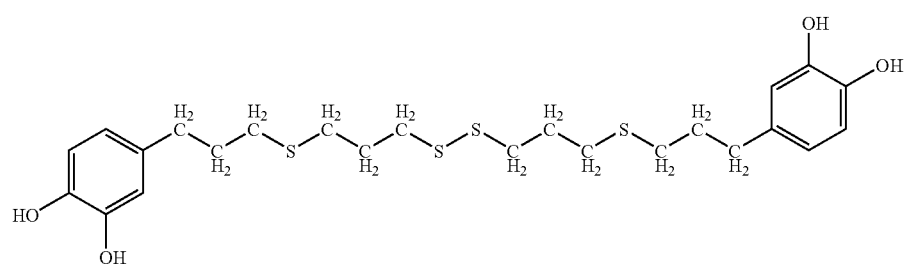
(XXI)
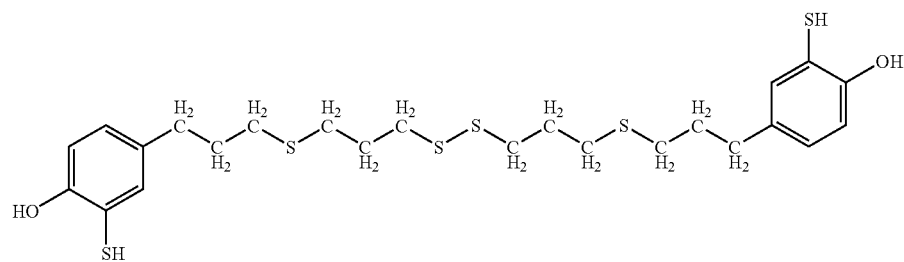

-continued
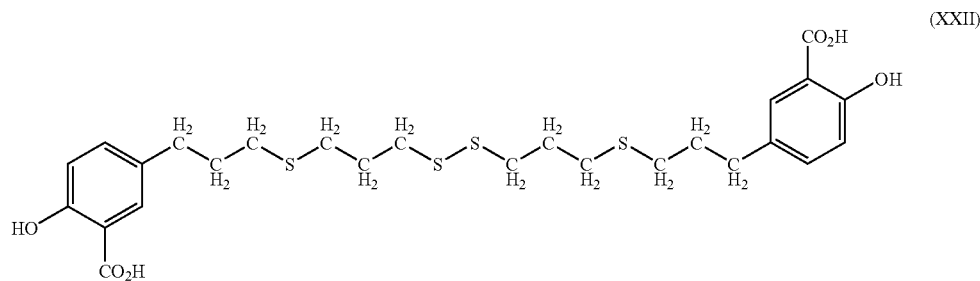
(XXII)
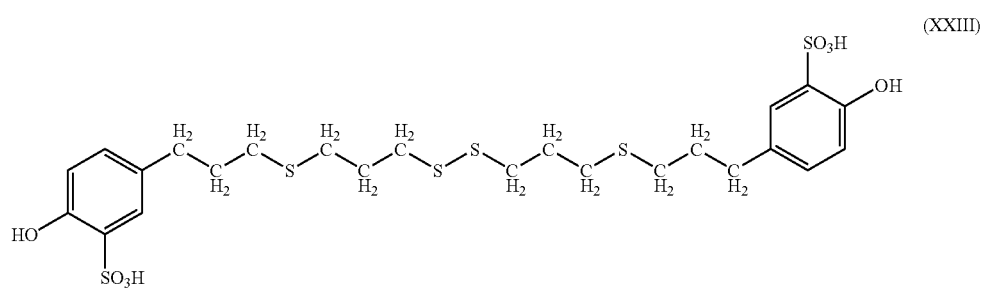
(XXIII)
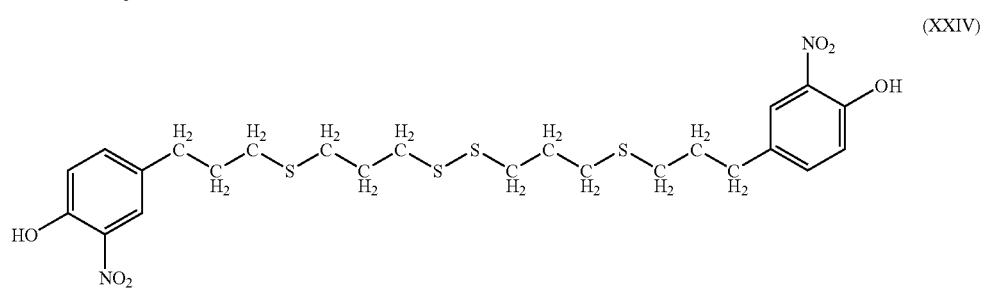
(XXIV)
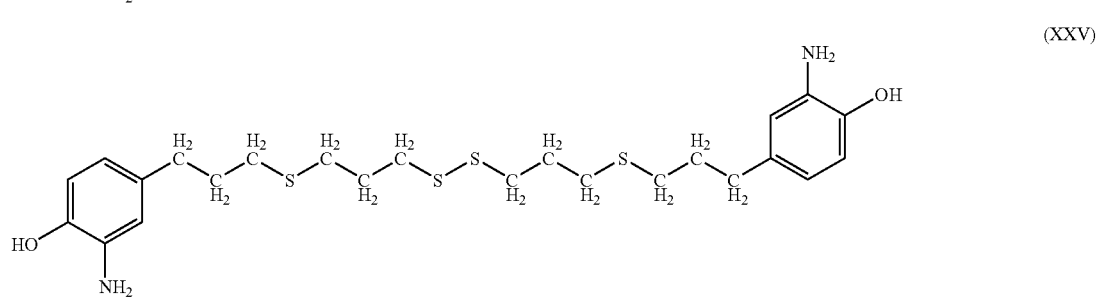
(XXV)
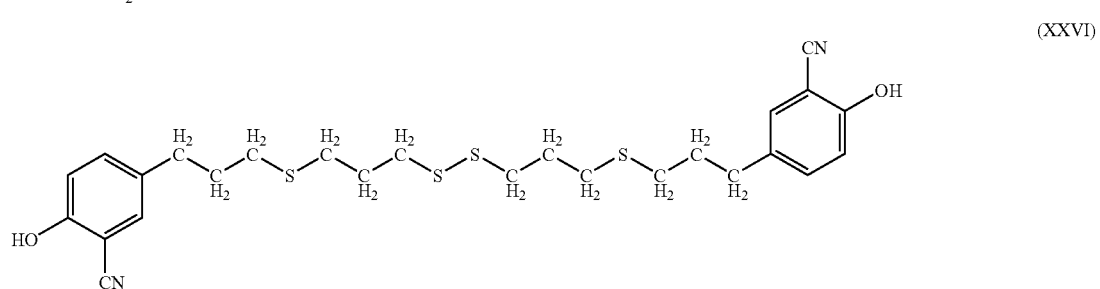
(XXVI)
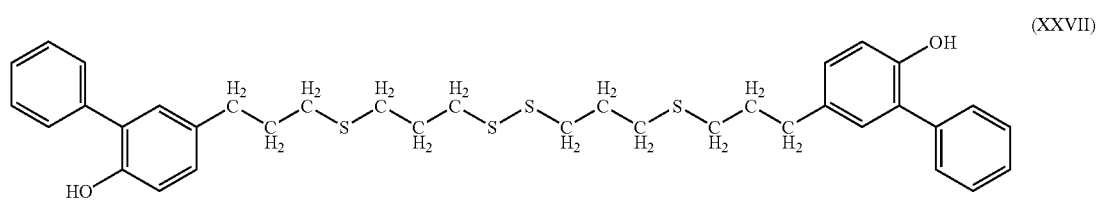
(XXVII)

-continued
(XXVIII)
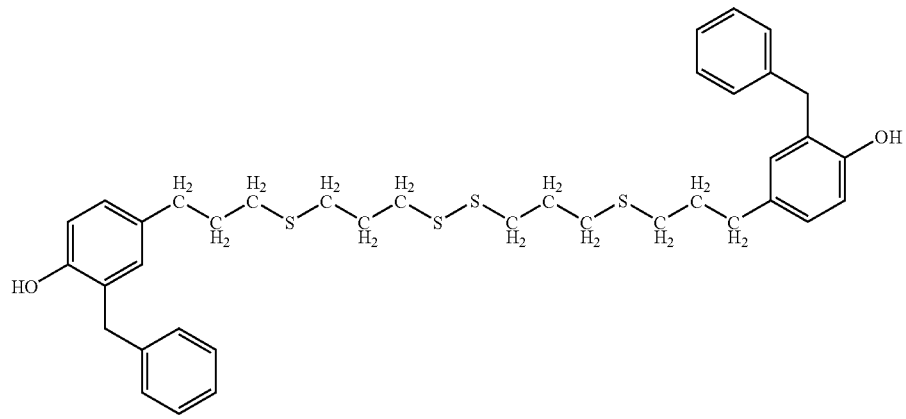
(XXIX)
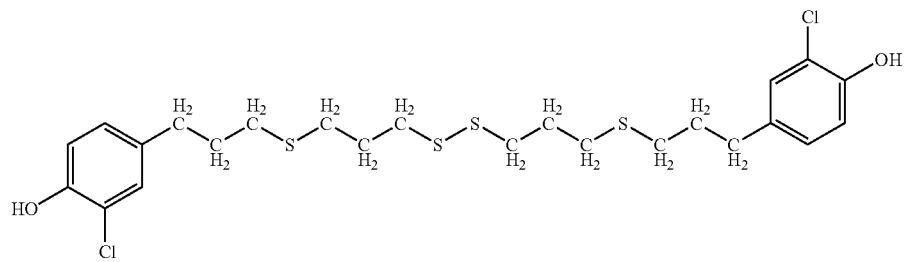
(XXX)
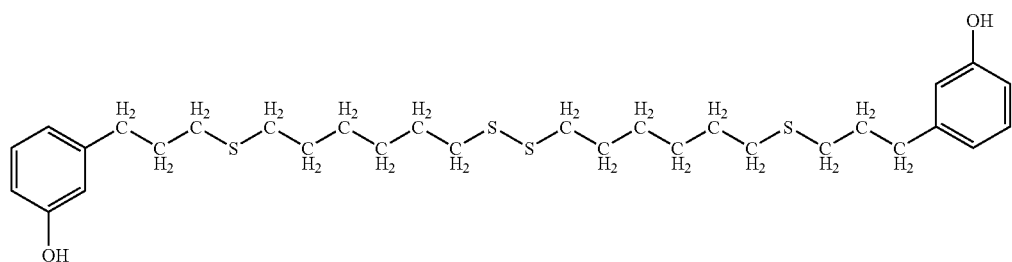
(XXXI)
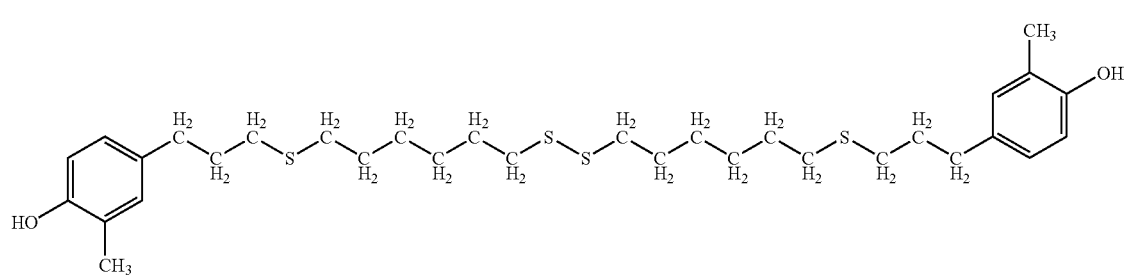
(XXXII)
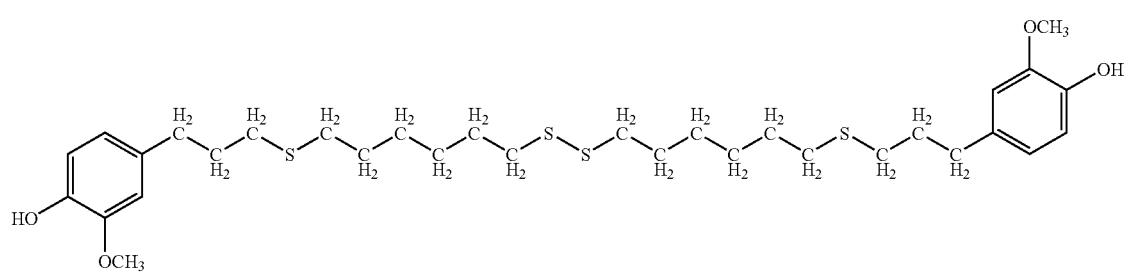

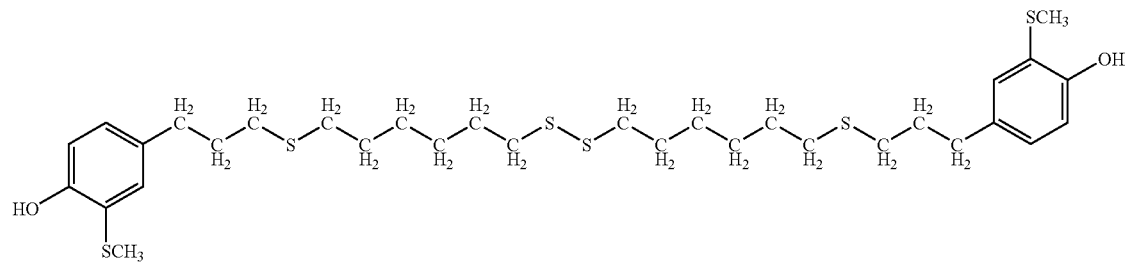
(XXXIII)
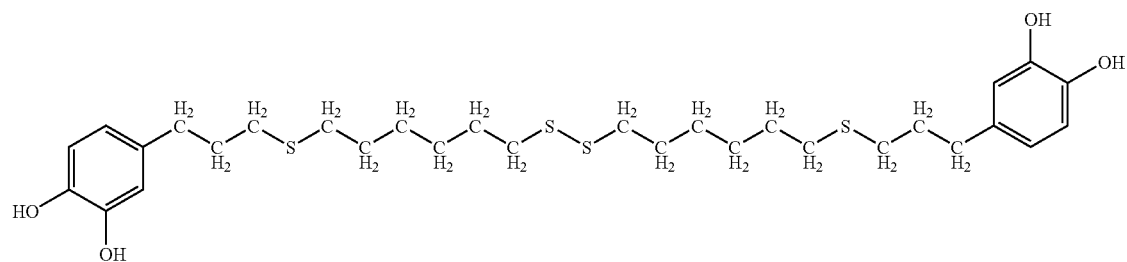
(XXXIV)
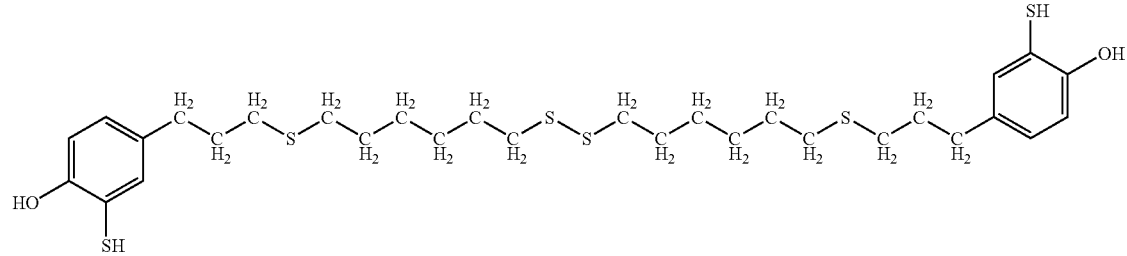
(XXXV)
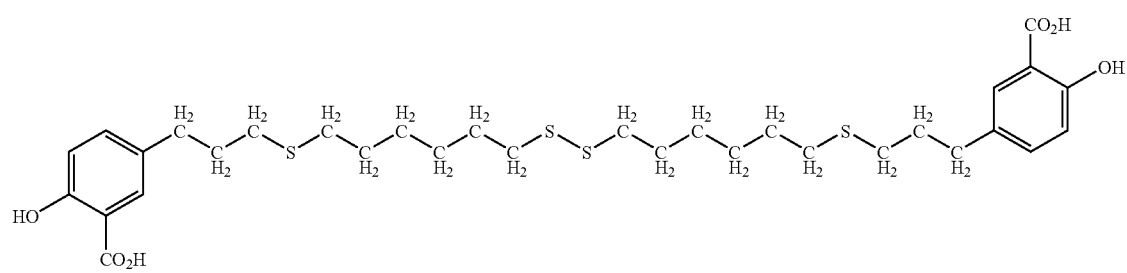
(XXXVI)
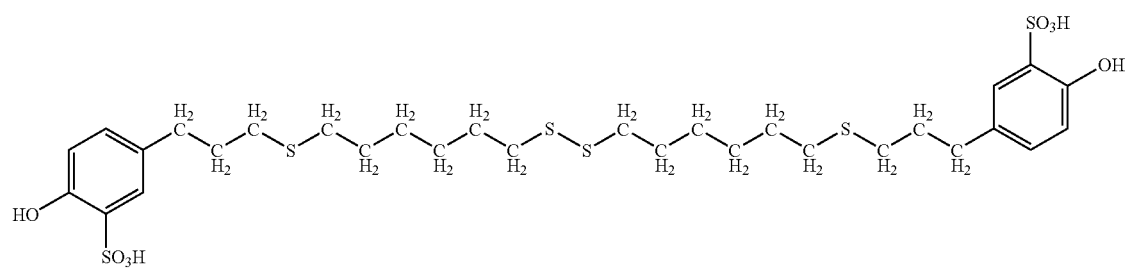
(XXXVII)

-continued
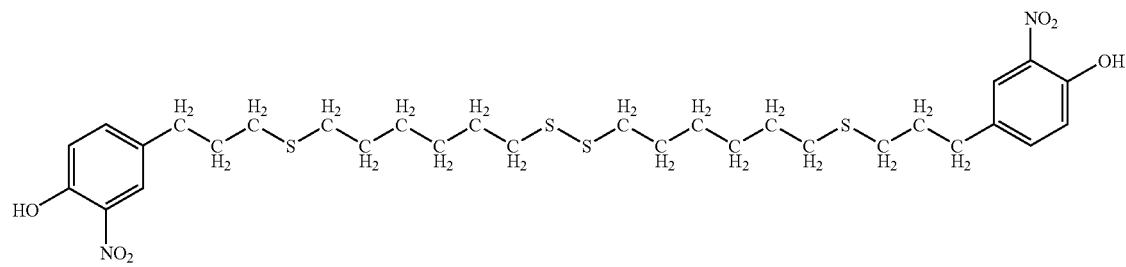
(XXXVIII)
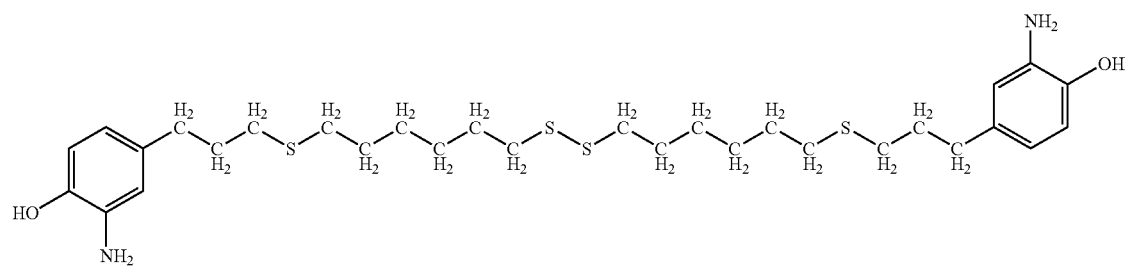
(XXXVIX)
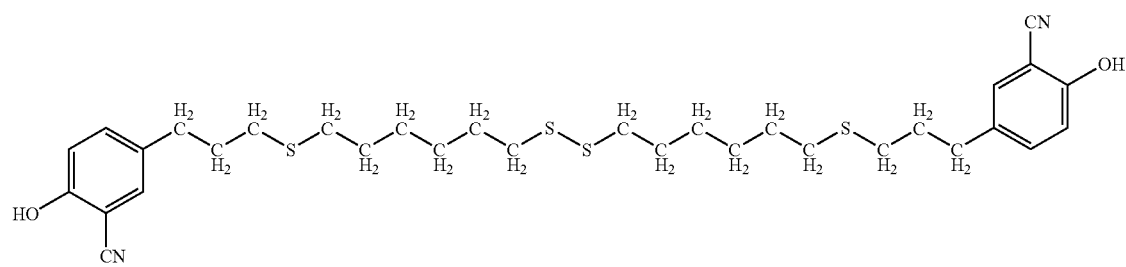
(XXXX)
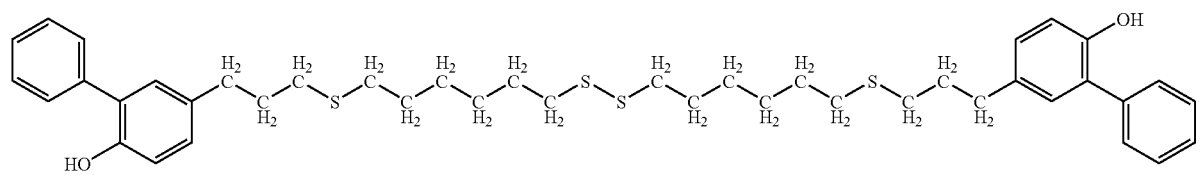
(XXXXI)
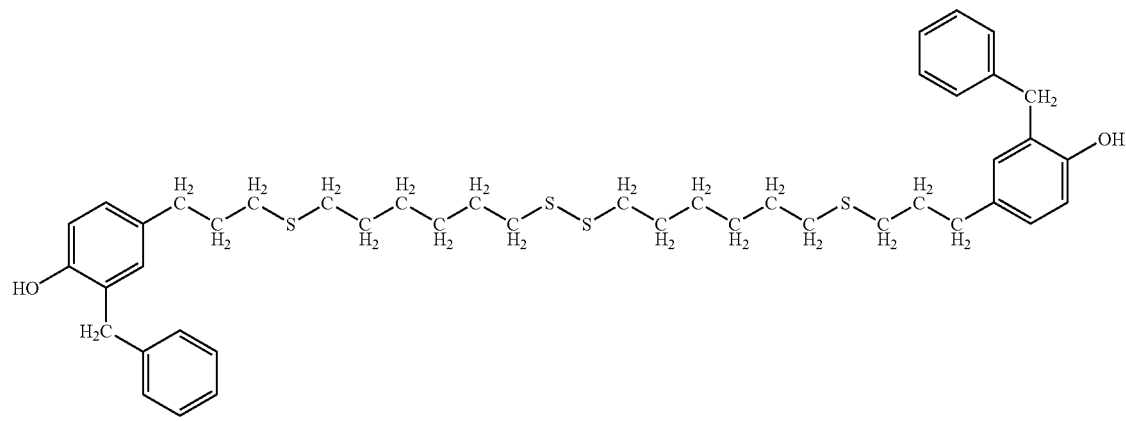
(XXXXII)

-continued

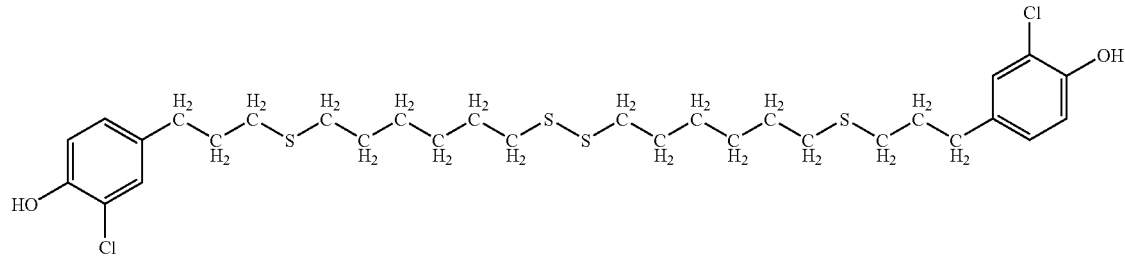

(XXXXIII)

As a method for producing the disulfide-containing phenolic resin represented by the above-mentioned general formula (5), the above-mentioned method may be mentioned.

The phenol compound represented by the above-mentioned general formula (7) or the above-mentioned general formula (8) and the dithol represented by the above-mentioned general formula (9) are reacted basically with an equal molar ratio at 100° C. to 200° C. for 30 minutes to 7 hours or so under heating, a reaction product including a phenolic resin containing disulfide precursor represented by the above-mentioned general formula (6) can be obtained. The precursor is isolated from the obtained reaction product and purified, or the reaction product is used as such, the material is subjected to oxidation reaction in a solvent by using hydrogen peroxide at 50° C. to 70° C. for 1 to 3 hours or so to produce a phenolic resin-containing disulfide.

Progress of the reaction can be confirmed by GPC or an infrared absorption spectrum.

When a phenolic resin other than the disulfide-containing phenolic resin represented by the above-mentioned the general formula (5) is used as (A) a curing agent, it is not particularly limited as the phenolic resin to be used in combination, and there may be mentioned, for example, a phenolic resin having 2 or more phenolic hydroxyl groups in one molecule generally used as a curing agent, and a novolac type phenolic resin obtained by reacting a phenol such as phenol, cresol, resorcine, catechol, bisphenol A, bisphenol F, phenylphenol, amino-phenol and the like and/or a naphthol such as α-naphthol, β-naphthol, dihydroxynaphthalene and the like with a compound having an aldehyde group such as formaldehyde, acetaldehyde, propionaldehyde, benzaldehyde, salicyl-aldehyde and the like to condensation or copolycondensation in the presence of an acidic catalyst; an aralkyl type phenolic resin such as a phenol-aralkyl resin, a naphthol-aralkyl resin and the like synthesized by a phenol and/or a naphthol with dimethoxy-para-xylene or bis(methoxymethyl)-biphenyl; a dicyclopentadiene type phenolic resin or a dicyclopentadiene type naphthol resin synthesized from a phenol and/or a naphthol with dicyclopentadiene by copolymerization; a terpene-modified phenolic resin; a biphenyl type phenolic resin; a triphenylmethane type phenolic resin and the like, and they may be used alone or in combination of two or more.

When a phenolic resin other than the phenolic resin containing disulfide represented by the above-mentioned the general formula (5) is used as (A) a curing agent, a formulation amount of the phenolic resin-containing disulfide represented by the above-mentioned general formula (5) is not specifically limited, and preferably 0.1 to 80% by weight, further preferably 1 to 50% by weight based on the total weight of (A) the curing agent. If the content of the phenolic resin-containing disulfide is less than 0.1% by weight, an improved effect in adhesive property tends to be little, while if it exceeds 80% by weight, strength of the epoxy resin composition tends to be lowered.

An equivalent ratio of (A) the curing agent containing the phenolic resin-containing disulfide represented by the above-mentioned the general formula (5) and (B) the epoxy resin, i.e., a ratio of the number of the hydroxyl groups in the curing agent/the number of the epoxy groups in the epoxy resin is not specifically limited, and preferably 0.6 to 1.5, further preferably 0.8 to 1.2.

As (B) the epoxy resin to be used in the present invention, it is not specifically limited with those generally employed. For example, there may be mentioned a novolac type epoxy resin which is obtained by expozidizing a novolac resin obtained by subjecting a phenol such as phenol, cresol, xylenol, resorcine, catechol, bisphenol A, bisphenol F and the like and/or a naphthol such as α-naphthol, β-naphthol, dihydroxynaphthalene and the like with a compound having an aldehyde group such as formaldehyde, acetaldehyde, propionaldehyde, benzaldehyde, salicyl-aldehyde and the like to condensation or copolycondensation in the presence of an acidic catalyst, including a phenol novolac type epoxy resin, an orthocresol novolac type epoxy resin, an epoxy resin having a triphenylmethane skeleton; a diglycidyl ether (bisphenol type epoxy resin) of a bisphenol such as bisphenol A, bisphenol F, bisphenol S and the like; a diglycidyl ether (biphenyl type epoxy resin) such as an alkyl-substituted or unsubstituted biphenol and the like; a stylbene type epoxy resin; a hydroquinone type epoxy resin; a glycidyl ester type epoxy resin obtained by the reaction of a polybasic acid such as phthalic acid, dimeric acid and the like with epichlorohydrine; a glycidylamine type epoxy resin obtained by the reaction of a polyamine such as diaminodiphenylmethane, isocyanuric acid and the like with epichlorohydrine; an epoxidized product (dicyclopentadiene type epoxy resin) of a polycondensed resin of dicyclopentadiene and a phenol; an epoxy resin (naphthalene type epoxy resin) having a naphthalene ring; an epoxidized product of an aralkyl type phenolic resin such as a phenol-aralkyl resin, a naphthol-aralkyl resin and the like; a trimethylolpropane type epoxy resin; a terpene-modified epoxy resin; a linear aliphatic epoxy resin obtained by oxidizing an olefin bond by a peracid such as peracetic acid and the like; an alicyclic epoxy resin; a sulfur atom-containing epoxy resin and the like. They may be used alone or in combination of two or more.

In the epoxy resin composition of the present invention, (C) a curing accelerator may be contained, if necessary. As the curing accelerator to be used, it is not specifically limited so long as it promotes the reaction of (A) the curing agent and (B) the epoxy resin, and there may be mentioned, for example, tertiary amines such as 1,8-diaza-bicyclo[5.4.0]undecene-7, 1,5-diaza-bicyclo[4.3.0]-nonane, 5,6-dibutylamino-1,8-diaza-bicyclo[5.4.0]undecene-7, benzyldimethylamine, triethanolamine, dimethylaminoethanol, tris (dimethylaminomethyl)phenol, etc. and derivatives thereof, imidazoles such as 2-methylimidazole, 2-phenylimidazole, 2-phenyl-4-methylimidazole, etc., and derivatives thereof, organic phosphines such as tributylphosphine, methyldiphenylphosphine, triphenylphosphine, diphenylphosphine, phenylphosphine, etc., phosphorus compounds having an intramolecular polarization in which a compound having a π bond such as maleic anhydride, benzoquinone, diazophenylmethane, etc. is added to the above-mentioned phosphines, tetraphenylborates such as tetraphenylphosphonium tetraphenylborate, tetraphenylphosphonium ethyltriphenylborate, tetrabutylphosphonium tetrabutylborate, 2-ethyl-4-methylimidazoletetraphenylborate, N-methylmorpholine tetraphenylborate, etc. and derivatives thereof and the like. They may be used alone or in combination of two or more.

A formulation amount of (C) the curing accelerator is not specifically limited so long as it is an amount that a curing-acceleration effect can be accomplished, and it is preferably 0.005 to 3 parts by weight based on 100 parts by weight of (B) the epoxy resin.

Also, in the epoxy resin composition of the present invention, an inorganic filler may be used, if necessary. The inorganic filler is to be formulated in the resin composition for the purpose of hygroscopicity, lowering linear expansion coefficient, improvement in thermal conductivity and improvement in strength, and there may be mentioned, for example, powder or spherical beads such as fused silica, crystalline silica, glass, alumina, zirconia, calcium silicate, calcium carbonate, silicon carbide, silicon nitride, aluminum nitride, boron nitride, beryllia, zirconia, potassium titanate, etc., monocrystalline fiber of potassium titanate, silicon carbide, silicon nitride, alumina, etc., glass fiber and the like, and examples of the inorganic filler having flame retardancy may include aluminum hydroxide, magnesium hydroxide, zinc borate and the like. They may be used alone or in combination of two or more.

Of these, fused silica is preferred in the viewpoint of lowering linear expansion coefficient, and alumina is preferred in the viewpoint of high thermal conductivity, and with regard to the shape of the filler, a spherical or near to spherical shape is preferred in the points of fluidity at the time of molding and mold wearability.

Moreover, as the other additives, a surface treating agent including a coupling agent such as an epoxysilane, an aminosilane, a ureidosilane, a vinylsilane, an alkylsilane, an organic titanate, an aluminum alcoholate, etc., a frame retardant including a nitrogen-containing compound such as a brominated epoxy resin, antimony trioxide, a phosphoric acid ester, a melamine resin, phosphazene, etc., a releasing agent such as a higher fatty acid, a higher fatty acid metal salt, an ester type wax, etc., a colorant such as carbon black, etc., a stress-relaxing agent such as silicone oil, silicone rubber, etc., may be formulated in the epoxy resin composition of the present invention, if necessary.

The epoxy resin composition in the present invention can be prepared by using any means so long as it can uniformly disperse and mix various kinds of starting materials, and as a general means, there may be mentioned a method in which starting materials with predetermined formulation amounts are sufficiently mixed by a mixer, etc., kneading the materials by a mixing roller, an extruder, etc., under fusion, and then, cooling and pulverizing.

In the present invention, an adhesive can be further prepared by using the epoxy resin composition of the pre-sent invention prepared as mentioned above. The adhesive of the present invention contains the above-mentioned epoxy resin composition of the present invention, and it may be the epoxy resin composition alone, or an additive such as a solvent, a dispersant, etc., may be optionally added to the epoxy resin composition, if necessary. Also, a shape of the adhesive can be made a tablet form, a film form, a sheet form, a tape form, a liquid form, a paste form, etc., depending on the uses.

For adhering a circuit of electric and electronic parts of a semiconductor package, etc. to a supporting member such as a lead flame, etc. by using the adhesive of the present invention, the adhesive is firstly coating on the supporting member using a dispense method, a screen printing method, a stamping method, etc., the circuit is adhered under pressure, and then, it is cured under heating by using a heating device such as an oven, a heat block, etc.

The epoxy resin composition/adhesive of the present invention can be applied to an adhesive for connecting circuits of electric and electronic parts such as a die bonding agent, a silver paste, a silver film, an anisotropic conductive adhesive or an adhesive film, etc., and a sealing agent, etc.

EXAMPLE

Synthetic Example 1

To 2-liters of a separable flask equipped with a stirrer, a condenser and a thermometer were charged 328 g of 4-allyl-2-methoxyphenol, 81 g of 37% formalin and 3 g of oxalic acid, and the mixture was raised to 100° C. in an oil bath. Reaction was continued at a reflux temperature for 3 hours, thereafter the mixture was concentrated under reduced pressure at 180° C. for 3 hours to remove the unreacted 4-allyl-2-methoxyphenol and to obtain a dinuclear material of 4-allyl-2-methoxyphenol.

To 2-liters of a separable flask equipped with a stirrer, a condenser and a thermometer were charged 50 g of the obtained dinuclear material of 4-allyl-2-methoxyphenol, 11.3 g of ethanedithiol and 1.42 g of benzoyl peroxide (BPO), and the mixture was raised to 100° C. in an oil bath and the reaction was continued for 8 hours. Thereafter, an unreacted material was removed at 150° C. under reduced pressure.

GPC chart of the obtained resin was shown in FIG. 1. Also, spectra of 2D (2 dimensional) of H—H codie and 2D (2 dimensional) of H—C of the obtained resin are shown in FIG. 2 and FIG. 3, respectively.

Figure 2:
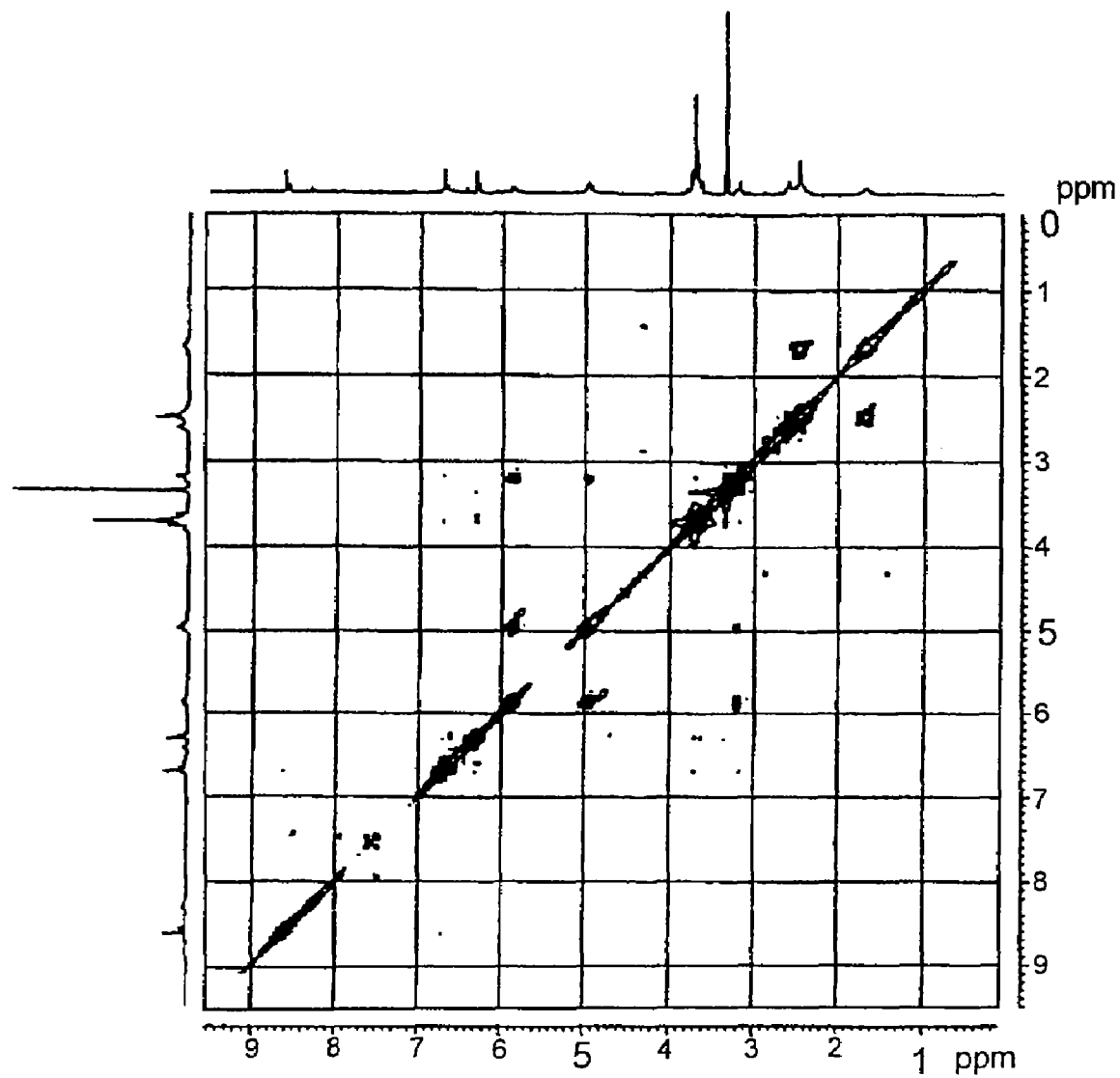
FIG. 2 shows a 2D (2 dimensional) NMR spectrum of H—H codie of the sulfur-containing phenolic resin obtained in Synthetic example 1.
Figure 3:
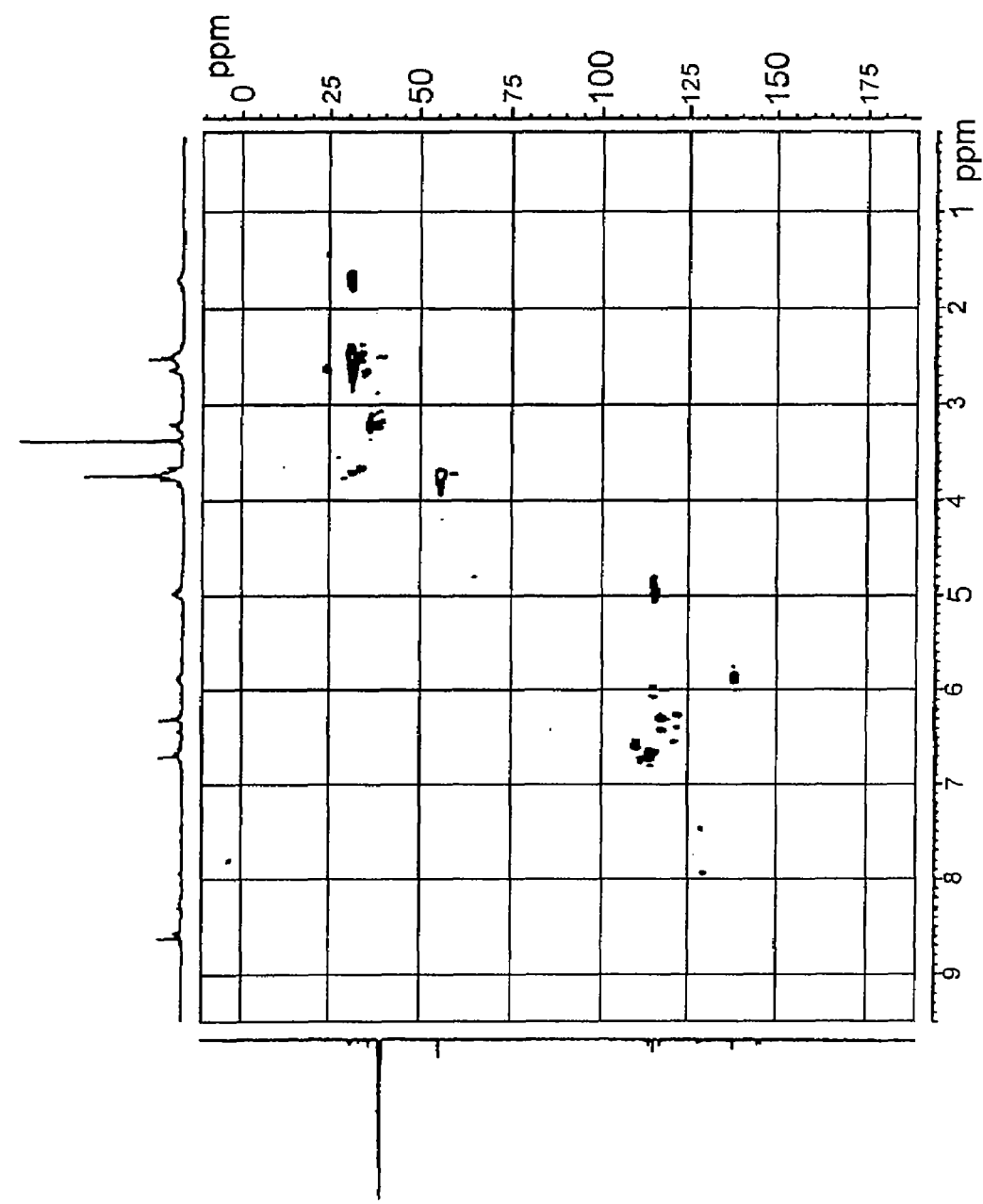
FIG. 3 shows a 2D (2 dimensional) NMR spectrum of H—C of the sulfur-containing phenolic resin obtained in Synthetic example 1.

From the results of NMR shown in FIG. 2 to FIG. 3, they show that the obtained resin has the molecular structure of the above-mentioned formula (13).

Synthetic Example 2

The operation to obtain the initial dinuclear material was carried out in the same manner as in Synthetic example 1.

Figure 4:
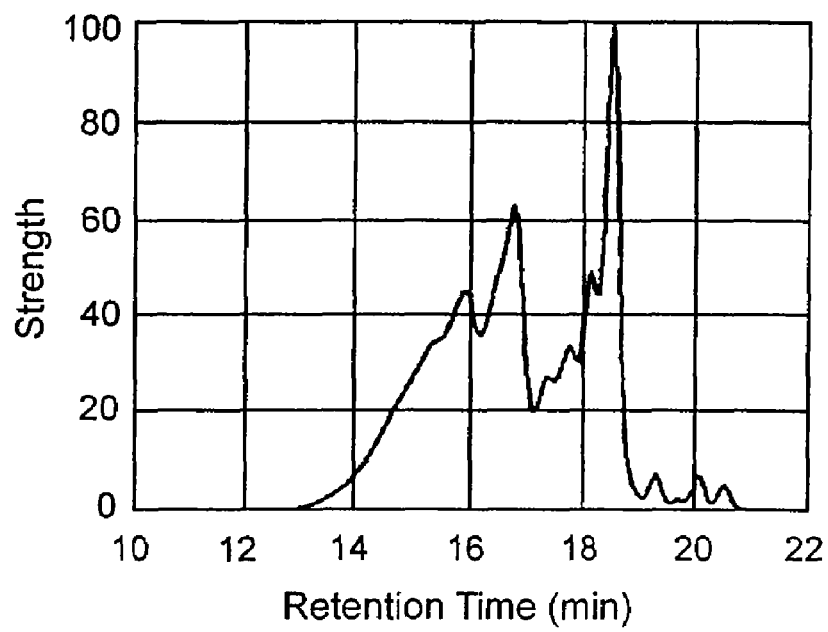
FIG. 4 shows a GPC chart of the resin obtained in Synthetic example 2.

To 2-liters of a separable flask equipped with a stirrer, a condenser and a thermometer were charged 90 g of a dinuclear material of 4-allyl-2-methoxyphenol, 19.1 g of ethanedithiol and 2.55 g of benzoyl peroxide, and the mixture was raised to 100° C. in an oil bath and the reaction was continued for 9 hours. Thereafter, an unreacted material was removed at 150° C. under reduced pressure. GPC chart of the obtained resin was shown in FIG. 4.

Synthetic Example 3

The operation to obtain the initial dinuclear material was carried out in the same manner as in Synthetic example 1.

Figure 5:
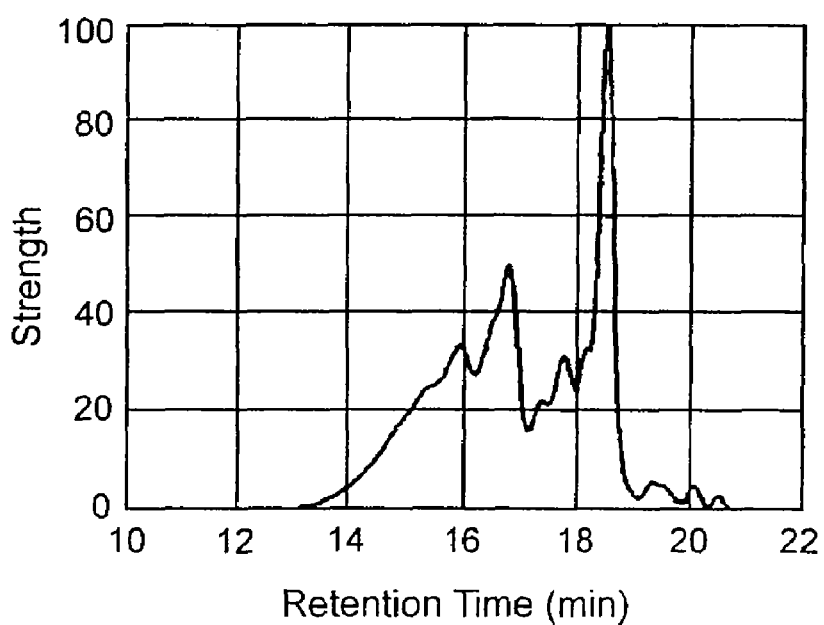
FIG. 5 shows a GPC chart of the resin obtained in Synthetic example 3.

To 2-liters of a separable flask equipped with a stirrer, a condenser and a thermometer were charged 90 g of a dinuclear material of 4-allyl-2-methoxyphenol and 16.9 g of ethanedithiol, and the mixture was raised to 100° C. in an oil bath and the reaction was continued for 12 hours. Thereafter, an unreacted material was removed at 150° C. under reduced pressure. GPC chart of the obtained resin was shown in FIG. 5.

Comparative Synthetic Example

To 2-liters of a separable flask equipped with a stirrer, a condenser and a thermometer were charged 94 g of phenol, 70 g of 37% formalin and 3 g of oxalic acid, and the mixture was raised to 100° C. in an oil bath. Reaction was continued at a reflux temperature for 3 hours, thereafter the mixture was concentrated under reduced pressure at 180° C. for 3 hours to remove the unreacted phenol and to obtain a phenol novolac resin.

<Evaluation of Resin Characteristics>

Characteristics of the sulfur-containing phenolic resins obtained in Synthetic example 1 to 3 were compared with those of Comparative Synthetic example and evaluated.

Measurements of a number average molecular weight (Mn) and a degree of polydispersion (Mw/Mn) were carried out by using high performance liquid chromatography L6000 manufactured by Hitachi Ltd. and a deta analyzing device C-R4A manufactured by Shimadzu Corporation. As GPC columns for analysis, G2000HXL+G3000HXL manufactured by Tosoh Corporation were used. A sample concentration was 0.2%, tetrahydrofuran was used as a mobile phase and the measurement was carried out with a flow rate of 1.0 ml/min. A calibration curve was prepared by using polystyrene standard samples, and the number average molecular weight and the like were measured by using the same.

Measurement of a nuclear magnetic resonance spectrum (NMR) was carried out by using AVANCE 500 manufactured by Bruker Instruments. Inc. As a solvent, deuterium-exchanged dimethylsulfoxide was used.

A melting viscosity was measured by using ICI Cone Plate Viscometer manufactured by REL (Research Equipment London Ltd). Under the conditions of a measurement temperature at 150° C., 0.1 to 0.3 g of the resin was placed on a hot plate, and a melting viscosity was measured at the conditions of lowering the position of the corn and allowed to stand for 1 minute.

The results are shown in Table 1.

TABLE 1

| Item | Synthetic example 1 | Synthetic example 2 | Synthetic example 3 | Comparative Synthetic example |
|---|---|---|---|---|
| Molecular weight | 828 | 815 | 743 | 810 |
| Degree of polydispersibility | 1.82 | 1.77 | 1.75 | 2.29 |
| Softening point (° C.) | 65 | 60 | 50 | 83 |

TABLE 1-continued

| Item | Synthetic example 1 | Synthetic example 2 | Synthetic example 3 | Comparative Synthetic example |
|---|---|---|---|---|
| ICI Viscosity (P) | 1.5 | 1.2 | 0.5 | 2.0 |

As shown in Table 1, the molecular weight of the sulfur-containing phenolic resin (Synthetic examples 1 to 3) of the present invention are the same as that of the phenol novolac resin (molecular weight 810) of Comparative Synthetic example, and they have characteristics that the softening point and the melting viscosity (ICI viscosity, poise) are low.

Example 1 Synthesis of phenolic monothiol
[Compound in which $R^6$ is an Ethylene Group Having a Carbon Number of 2 Among the Phenol Derivatives of the Formula (27)]

Figure 6:
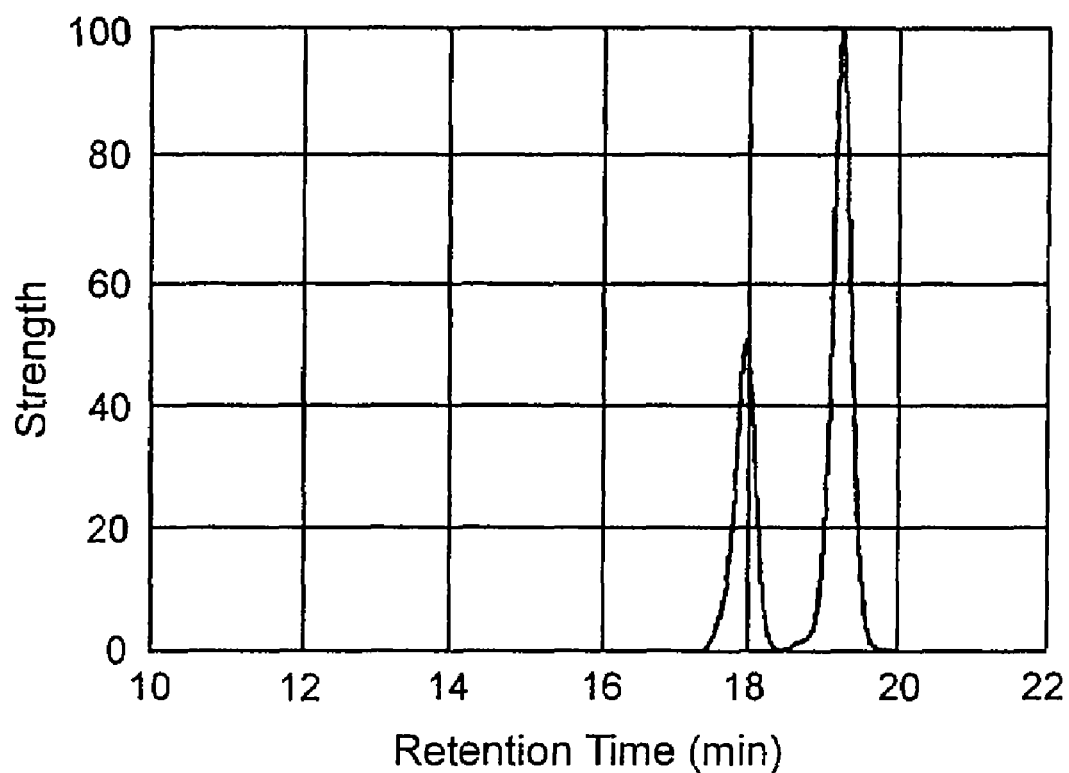
FIG. 6 shows a GPC chart of the reaction product (phenolic monothiol) obtained in Example 1.

In a separable flask was weighed 74.0 g (0.536 mol) of 2-allylphenol, and 50.5 g (0.536 mol) of ethanedithiol was added thereto. At a lid (separable cover) side of a four-necked separable flask were attached a reflux condenser and a stirring rod with stirring blades, and the stirring rod was connected to a motor for stirring through a stirring seal. At this state, the mixture was started to heating at 150° C. on an oil bath while stirring. Under reflux conditions, the mixture was maintained for about 4 hours. GPC of the reaction product was shown in FIG. 6. Two peaks are present, and the initially appeared peak (left peak) is a by-product and the secondary appeared peak (right peak) is a monothiol material.

Figure 7:
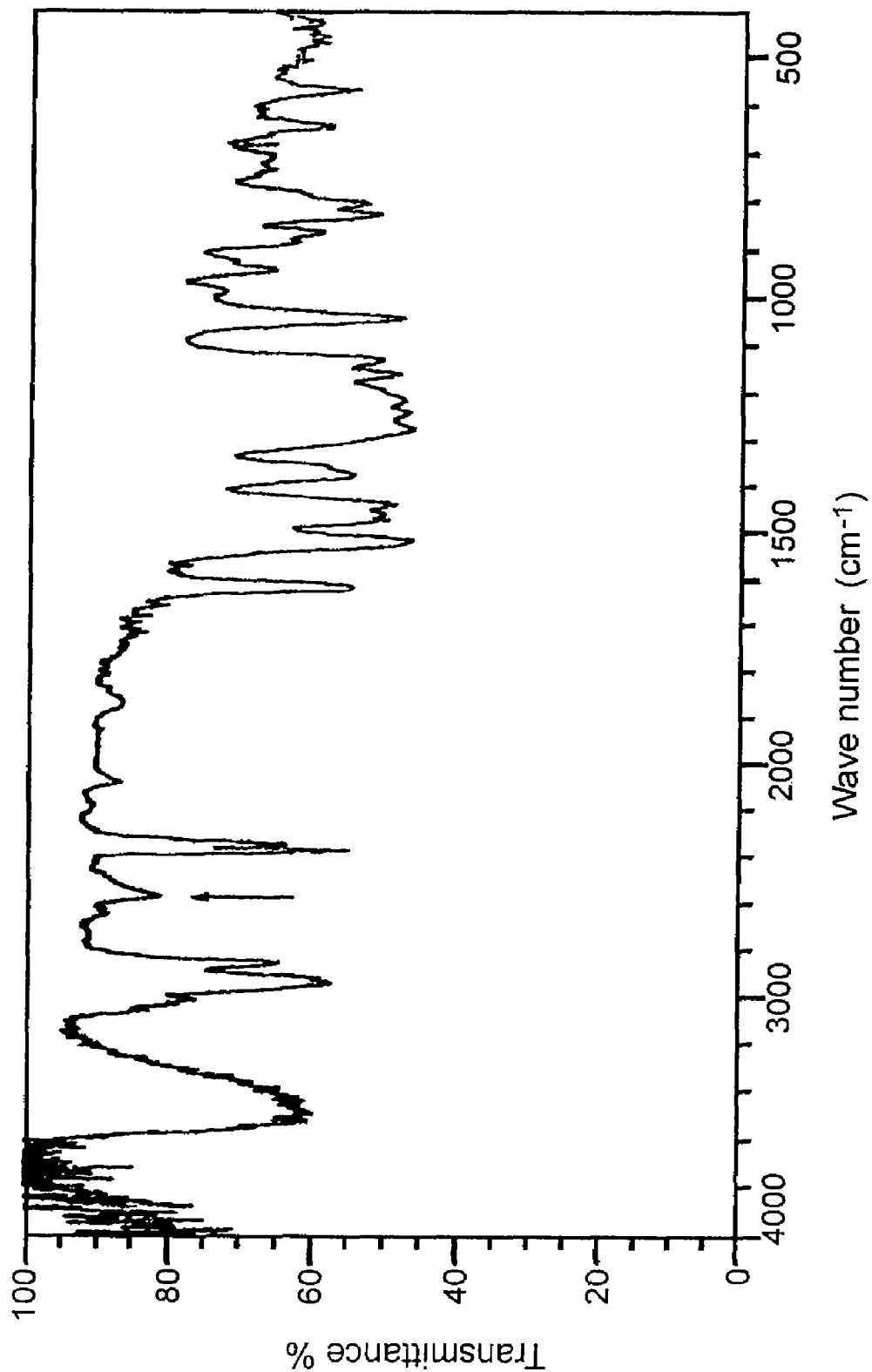
FIG. 7 shows an IR measurement chart of the reaction product (phenolic monothiol) in Example 1.

Also, an infrared absorption spectrum of the reaction product was shown in FIG. 7. An absorption peak deribed from a thiol (SH) can be admitted at around 2550 $cm^{-1}$.

Example 2 Synthesis of Phenolic Disulfide
[Compound in which $R^6$ is an Ethylene Group Having a Carbon Number of 2 Among the Phenol Derivatives of the Formula (24)]

Figure 8:
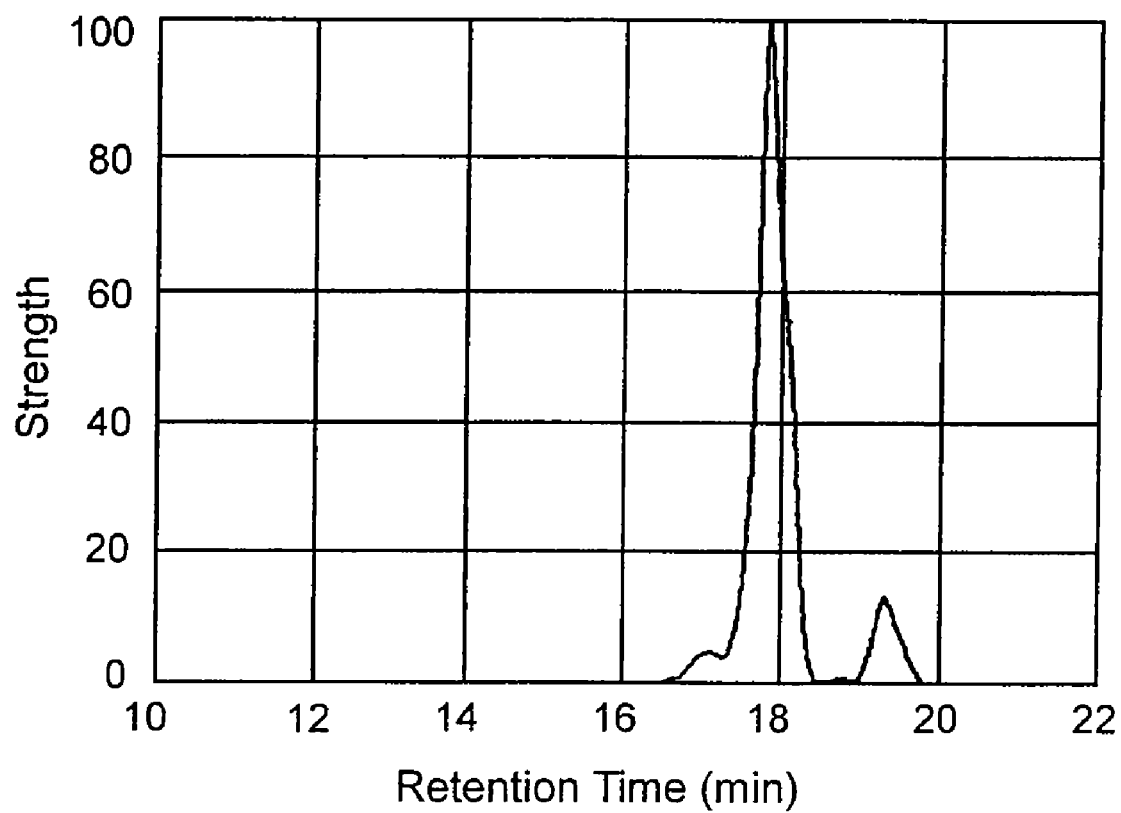
FIG. 8 shows a GPC chart of the reaction product (phenolic monothiol) obtained in Example 2.

In a separable flask was weighed 35 g (a molar amount of the monothiol is 0.1 mol) of the phenolic monothiol (content: 65%) obtained in Example 1, and a 30% aqueous hydrogen peroxide solution (about 3.4 ml) diluted 2-fold with ethanol was gradually added dropwise thereto. Thereafter, the mixture was heated at about 70° C. while stirring. Progress of the reaction was traced by GPC. After completion of the reaction, the reaction product was extracted with acetone and distilled water, and concentrated by an evaporator. GPC of the concentrated product was shown in FIG. 8. There are two peaks, and the initially appeared large peak (left peak) was a peak of a phenolic disulfide, and the secondary appeared peak (right peak) was a peak of a monothiol material. From these results, it can be understood that the monothiol is reacted with the disulfide. Incidentally, the peak of the disulfide is slightly different from the appeared position of the peak of the by-product shown in FIG. 6.

Figure 9:
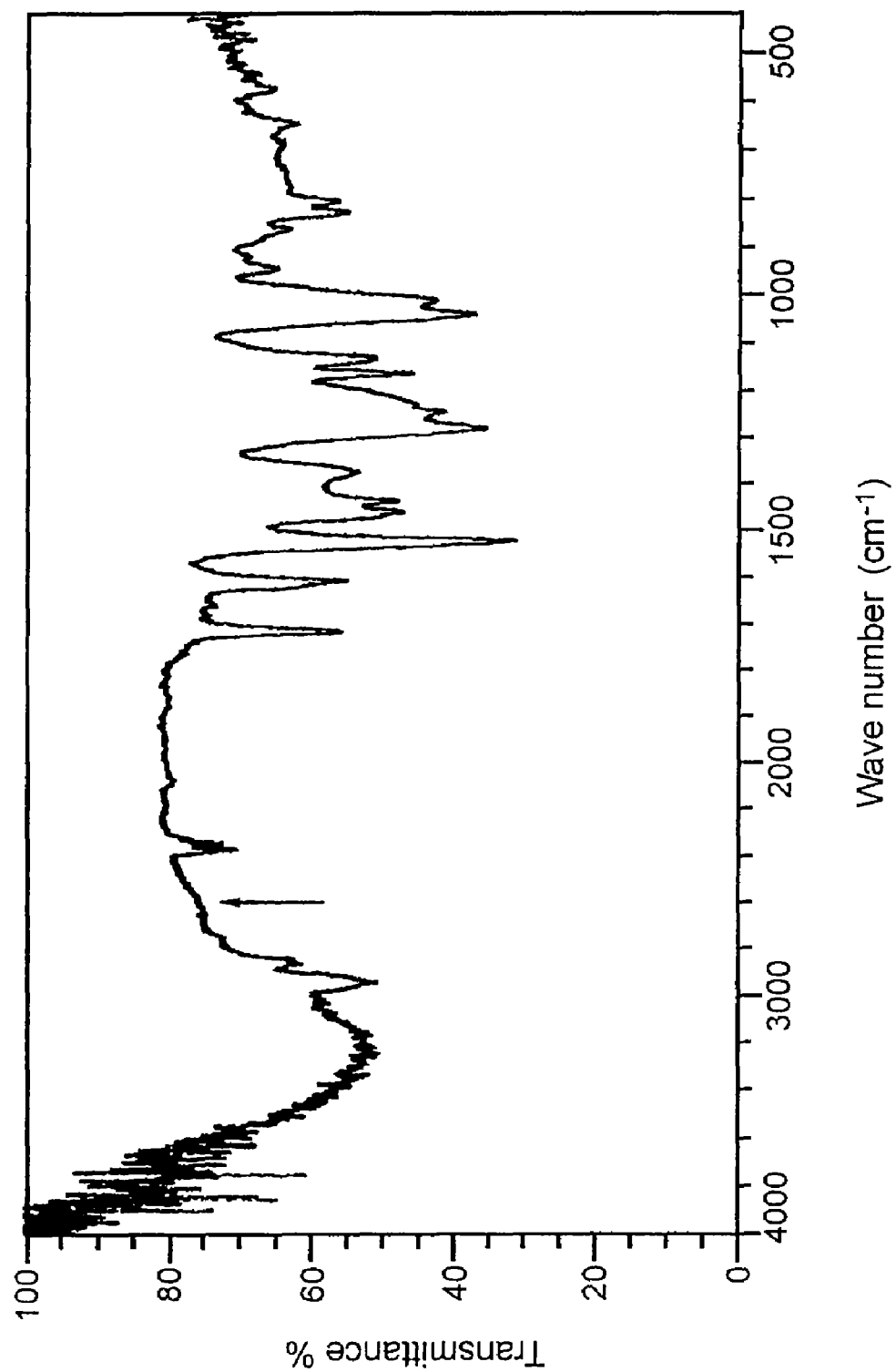
FIG. 9 shows an IR measurement chart of the reaction product (phenolic disulfide) in Example 2.

An infrared absorption spectrum of the concentrated product was shown in FIG. 9. Since the absorption peak derived from the thiol (SH) at around 2550 cm$^{-1}$ is disappeared, it can be understood that the thiol is reacted to be a disulfide.

Application Example

Application to an Adhesive (Synthesis of Polyimide Resin)

In a 1-liter fournecked flask equipped with a stirrer, a nitrogen-introducing tube and a drying tube was charged 41.0 g (0.10 mol) of 2,2-bis(4-(4-aminophenoxy)-phenyl)propane, and under nitrogen stream, 250 g of NMP (N-methylpyrrolidone) was added to the material to prepare a solution. The flask was moved on a water bath, and 41.0 g (0.10 mol) of 1,2-(ethylene)bis(trimellitate dianhydride) was added to the solution little by little under vigorous stirring. When the acid dianhydride was substantially dissolved, the mixture was reacted for 6 hours while gently stirring to obtain a polyamide solution.

Next, a distillation device was mounted to the four-necked flask in which the above-mentioned polyamide solution was charged, and 220 g of xylene was added thereto. Under nitrogen stream, the mixture was vigorously stirred on an oil bath of 180° C., and condensed water formed by imidation was azeotropically removed with xylene. The reaction mixture was poured into water, and a precipitated polymer was collected by filtration and dried to obtain a polyimide.

(Varnish Preparation)

To 100 parts by weight of the obtained polyimide were formulated 500 parts by weight of DMAc (dimethylacetamide) and 200 parts by weight of TCG-1 (filler) to prepare a polyimide varnish, and at this point, 5 parts by weight of the phenolic disulfide obtained in Example 2 was formulated thereto.

(Preparation of Adhesive Film)

The above-mentioned varnish was coated on a polypropylene film substrate with a thickness of 30 to 50 μm, dried by heating at 80° C. for 10 minutes, and then, at 150° C. for 30 minutes, cooled in a room temperature, and the dried product was peeled off from the substrate to obtain an adhesive film (test piece A). Incidentally, an adhesive film (test piece B) prepared in the same manner as mentioned above without adding the above-mentioned phenolic disulfide was used as a comparative (control).

(Evaluation of Adhesive Film)

With regard to the adhesive films obtained by the above-mentioned method, peeling adhesive force (peeling strength) was measured.

The adhesive film was cut to a size of 5 mm×5 mm, and this film was sandwiched between a silicon chip and a copper lead frame both having a size of 5 mm×5 mm, and a load of 1 kg was applied thereto and adhered by pressure at 180° C. or 250° C., and heated at 180° C. for one hour to cure the adhesive film. Peeling strength at 245° C. or 275° C. for 20 seconds-heating was measured by a push-pull gauge.

(Evaluation Results)

The measured results are shown in Table 2.

TABLE 2

| Item | Test piece A | Test piece B (Comparative) |
|---|---|---|
| Peeling strength (180° C. pressure contact) | 1.5 (measured at 245° C.) 1.7 (measured at 275° C.) | 0.3 (measured at 245° C.) 0.1 (measured at 275° C.) |

TABLE 2-continued

| Item | Test piece A | Test piece B (Comparative) |
|---|---|---|
| (250° C. pressure contact) | 1.9 (measured at 245° C.) 1.8 (measured at 275° C.) | 0.2 (measured at 245° C.) 0.1 (measured at 275° C.) |

Peeling strength of the adhesive film (test piece B) to which no phenolic disulfide had been formulated was 0.3 (measured at 245° C.) and 0.1 (measured at 275° C.) with 180° C. pressure-bonding, and 0.2 (measured at 245° C.) and 0.1 (measured at 275° C.) with 250° C. pressure-bonding, while peeling strength of the adhesive film (test piece A) to which the phenolic disulfide had been formulated was 1.5 (measured at 245° C.) and 1.7 (measured at 275° C.) with 180° C. pressure-bonding, and 1.9 (measured at 245° C.) and 1.8 (measured at 275° C.) with 250° C. pressure-bonding whereby the peeling strength was improved.

Next, a disulfide-containing phenolic resin to be used in Example was synthesized as mentioned below. Incidentally, progress of the reaction step was traced by using GPC (trade name: C-R4A) manufactured by Shimadzu Corporation, with columns: TSK gel G3000H$_{XL}$ and TSK gel G2000H$_{XL}$ both trade names manufactured by Tosoh Corporation, tetrahydrofuran (THF) as an eluent, a measurement concentration: 2.0 g/L, IR monitor: L-3300, trade name, manufactured by Hitachi Ltd., and a pump: L-6000, trade name, manufactured by Hitachi Ltd.

Example 3

Figure 10:
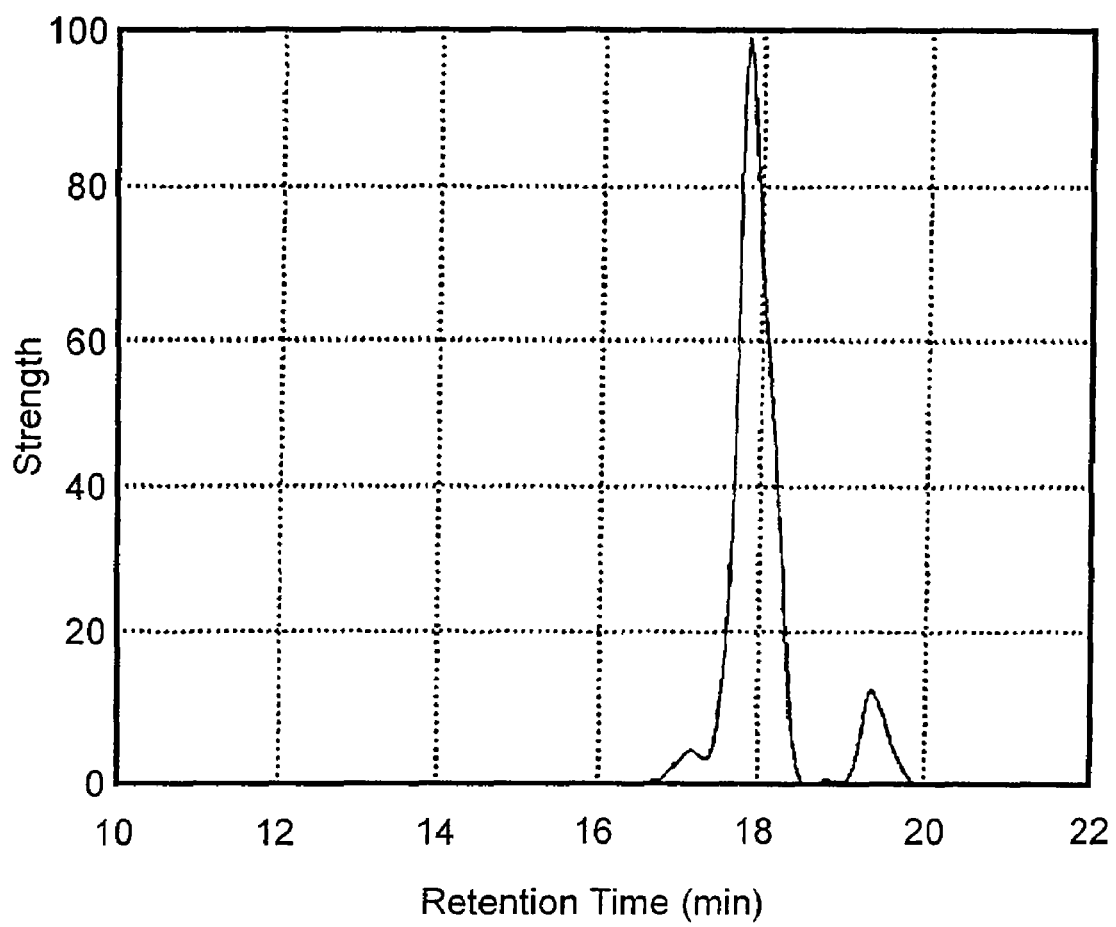
FIG. 10 shows a GPC chart of the resin containing a disulfide-containing phenolic resin precursor obtained in Example 3.
Figure 11:
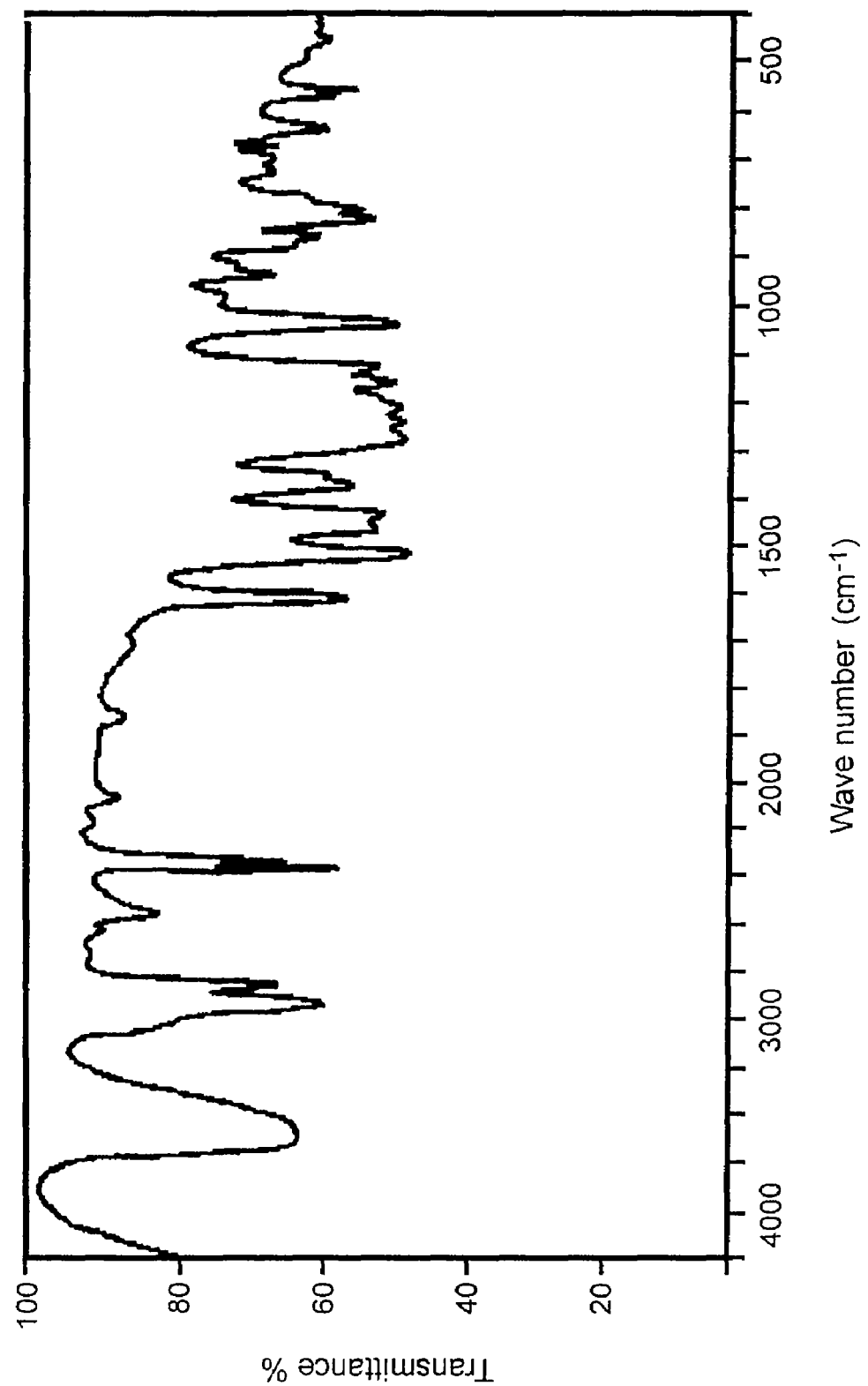
FIG. 11 shows an IR spectrum of the reaction product in FIG. 10.

Synthesis of Disulfide-Containing Phenolic Resin [General Formula (IV)] Precursor In a separable flask was weighed 90.6 g (0.536 mol) of eugenol, and 50.5 g (0.536 mol) of ethanedithiol was added thereto. At a lid (separable cover) side of a four-necked separable flask were attached a reflux condenser and a stirring rod with stirring blades, and the stirring rod was connected to a motor for stirring through a stirring seal. At this state, the mixture was started to heating at 150° C. on an oil bath while stirring. Under reflux conditions, the mixture was maintained for about 4 hours. GPC of the reaction product was shown in FIG. 10. Two peaks are present, and the initially appeared peak (left peak) is a by-product and the secondary appeared peak (right peak) is a thiol precursor. Also, an infrared absorption spectrum of the reaction product is shown in FIG. 11. An absorption peak derived from the thiol (SH) can be admitted at around 2550 cm$^{-1}$.

(Synthesis of Disulfide-Containing Phenolic Resin [General Formula (IV)])

Figure 12:
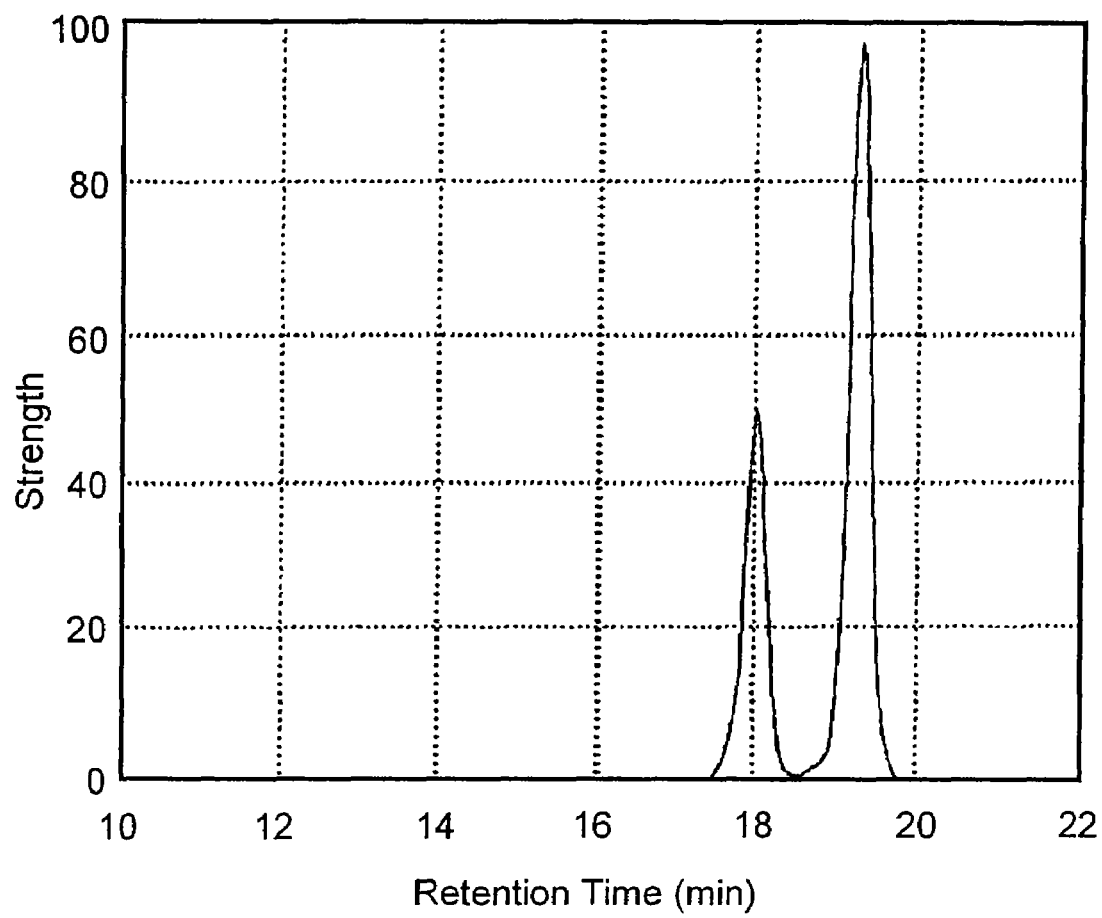
FIG. 12 shows a GPC chart of the concentrated product containing a disulfide-containing phenolic resin obtained in Example 3.

In a separable flask was weighed 35 g (a molar amount of the monothiol is 0.1 mol) of the reaction product (precursor content: 65%) containing the precursor obtained as mentioned above, a 30% aqueous hydrogen peroxide solution (about 3.4 ml) diluted 2-fold with ethanol was gradually added dropwise thereto. Thereafter, the mixture was heated at about 70° C. while stirring. After completion of the reaction, the reaction product was extracted with acetone and distilled water, and concentrated by an evaporator. GPC of the concentrated product was shown in FIG. 12. There are two peaks, and the initially appeared large peak (left peak) was a peak of a phenolic disulfide, and the secondary appeared peak (right peak) was a peak of a monothiol material. From these results, it can be understood that the monothiol is reacted with the disulfide. Incidentally, the peak of the disulfide is slightly different from the appeared position of the peak of the by-product shown in FIG. 10.

Figure 13:
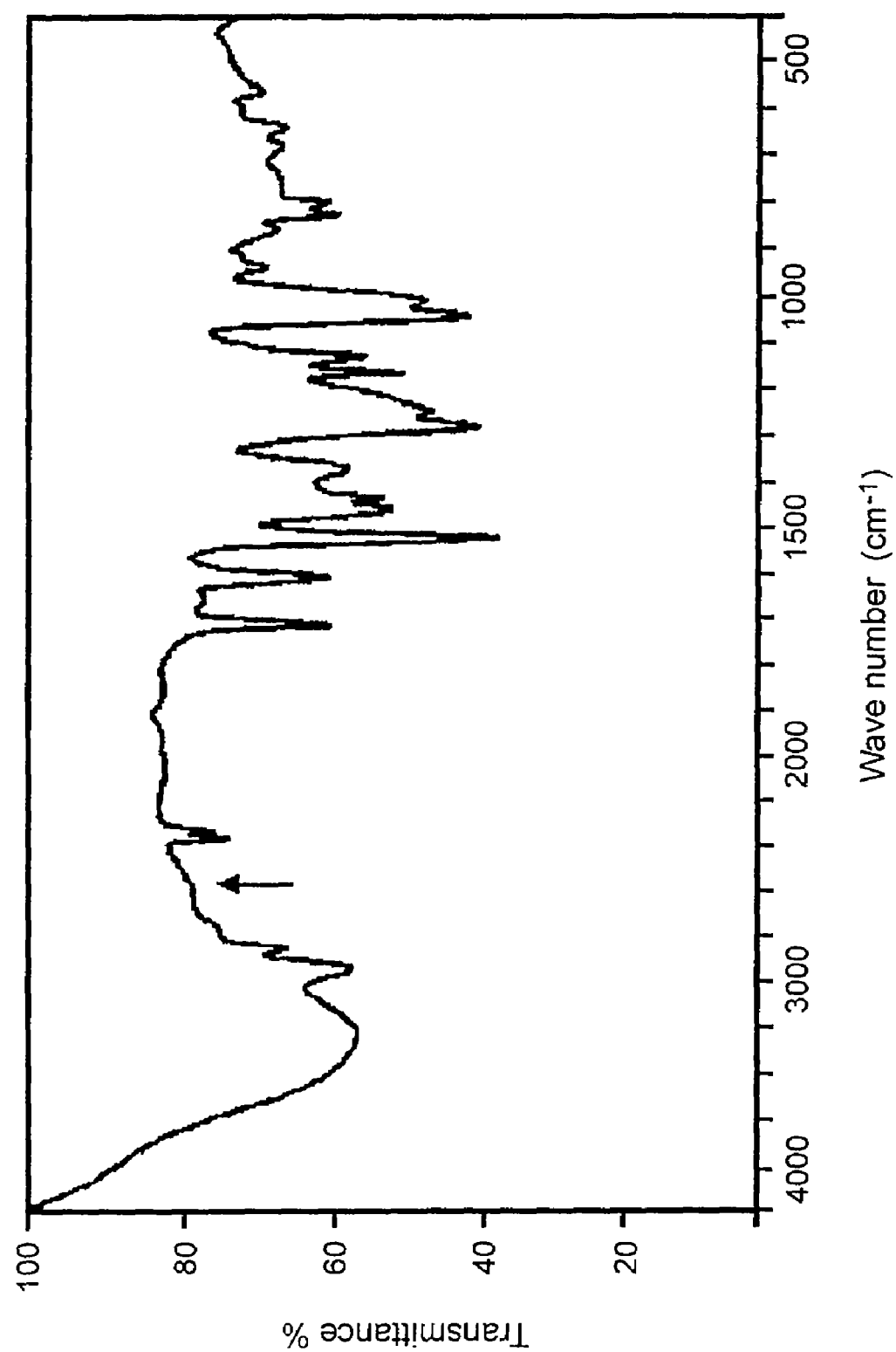
FIG. 13 shows an IR spectrum of the concentrated product in FIG. 12.

An infrared absorption spectrum of the concentrated product was shown in FIG. 13. Since the absorption peak derived from the thiol (SH) at around 2550 $cm^{-1}$ is disappeared, it can be understood that the thiol is reacted to be a disulfide.

Example 4

Synthesis of Disulfide-Containing Phenolic Resin [General Formula (XVIII)]

Experiment was carried out completely the same manner as in Example 3 except for adding 58.0 g of propanedithiol in place of 50.5 g of ethanedithiol.

Example 5

Synthesis of Disulfide-Containing Phenolic Resin [General Formula (XXXII)]

Experiment was carried out completely the same manner as in Example 3 except for adding 80.6 g of hexanedithiol in place of 50.5 g of ethanedithiol.

Examples 6 to 8 and Comparative Example 1

Respective materials were weighed with formulation ratio shown in Table 3 by using the disulfide-containing phenolic resins (Example 6: General formula (IV), Example 7: General formula (XVIII), Example 8: General formula (XXXII)) obtained in the above-mentioned Examples 3 to 5, a phenol.aralkyl resin (MEH7800SS, trade name, available from Meiwa Plastic Industries, Ltd.), and a melamine-modified phenolic resin (KA-7052, trade name, available from Dainippon Ink & Chemicals Incorporated) as (A) curing agents, a biphenyl type epoxy resin (YX4000, trade name, available from Japan Epoxy Resin Co., Ltd.) and a novolac type brominated epoxy resin (BREN105, trade name, available from Nippon Kayaku Co., Ltd.) as (B) epoxy resins, an adduct of triphenylphosphine and p-benzoquinone as (C) a curing accelerator, and polyethylene oxide (a releasing agent, PED153, trade name, available from Clariant Japan K.K.) as the other additive. On a stainless vat processed with fluorine, and on a hot plate at 100° C., materials other than the curing accelerator were firstly mixed and kneaded for about 2 minutes, then, the curing accelerator was added to the mixture and they were rapidly mixed within 30 seconds uniformly, and cooled to room temperature to obtain epoxy resin compositions of Examples 6 to 8 and Comparative example 1.

TABLE 3

| | Formulation (g) | | | |
|---|---|---|---|---|
| Name of materials | Comparative example 1 | Example 6 | Example 7 | Example 8 |
| Phenol resin containing disulfide | — | 4.0 | 4.0 | 4.0 |
| MEH7800SS | 77.4 | 77.4 | 77.4 | 77.4 |
| KA-7052 | 6.0 | 6.0 | 6.0 | 6.0 |
| YX4000 | 82.0 | 82.0 | 82.0 | 82.0 |
| BREN105 | 18.0 | 18.0 | 18.0 | 18.0 |
| Curing accelerator | 3.0 | 3.0 | 3.0 | 3.0 |
| PED153 | 3.0 | 3.0 | 3.0 | 3.0 |

180° peeling strength of the obtained epoxy resin compositions was measured by the method as shown below. The results are shown in Table 4.

At a tip of copper lead frame (length: 5 cm, width: 0.8 cm) to which nickel, palladium and gold were deposited in this order was coated each of the epoxy resin compositions of Example 6 to 8 and Comparative example 1, the same kind of lead frame was so contact-bonded thereon that an adhesion area became about 40 $mm^2$, heated on a hot plate at 200° C. for 2 minutes, and further cured in an oven at 175° C. for 5 hours. Peeling strengths at 265° C. of the resulting materials were measured by using Tensilon RTM-100 (Peeling rate: 0.5 mm/minute) manufactured by Orientec Corporation. Measured results are shown with an average of the measured values carried our 20 times with regard to respective samples. Incidentally, the measured results are converted into an adhesion area of 10.75 $mm^2$.

TABLE 4

| Evaluated items | Comparative example 1 | Example 6 | Example 7 | Example 8 |
|---|---|---|---|---|
| Peeling strength (N) | 10.5 | 11.8 | 10.9 | 11.5 |
| Peeling energy (Nm) | $5.8 \times 10^{-4}$ | $7.2 \times 10^{-4}$ | $6.6 \times 10^{-4}$ | $7.0 \times 10^{-4}$ |

UTILIZABILITY IN INDUSTRY

The sulfur-containing phenolic resin of the present invention is a novel phenolic resin, and the resin itself is soft so that it is not a brittle (having flexibility) phenolic resin. It can be considered to be applied for the uses such as a resin for molding materials or an epoxy resin-curing agent excellent in electric insulating property or adhesive property, and an adhesive, an adhesive film, an anisotropic conductive film and the like.

According to the process of the present invention, the above-mentioned sulfur-containing phenolic resin can be produced easily.

The phenol derivatives of the formula (5) of the present invention is a novel compound.

The phenol derivatives of the formula (6) of the present invention is also a novel compound, and can be a synthetic intermediate of the phenol derivatives of the above-mentioned formula (5).

According to the process for preparing the phenol derivatives of the formula (6) of the present invention, the phenol derivatives of the formula (6) can be synthesized easily.

According to the process for preparing the phenol derivatives of the formula (5) of the present invention, the phenol derivatives of the formula (6) can be synthesized easily.

When the phenol derivatives of the formula (6) obtained by the present invention is formulated into a resin-type adhesive, it shows excellent adhesive force onto a surface layer covered by a metal material. They can be a useful additive for a semiconductor mounting technology.

The epoxy resin composition of the present invention is, as shown in Examples, excellent in adhesive strength to a surface layer coated with a metallic material as compared with the epoxy resin composition containing no disulfide-containing phenolic resin. Therefore, it can be utilized as an adhesive material for electronic materials such as a semiconductor package and the like. The adhesive of the present invention contains the epoxy resin composition of the present invention, so that it can be applied for a circuit connection of electric and electronic parts such as a semiconductor package and the like, and shows good adhesive strength.

The invention claimed is:

1. A phenol derivatives represented by the following formula (5):

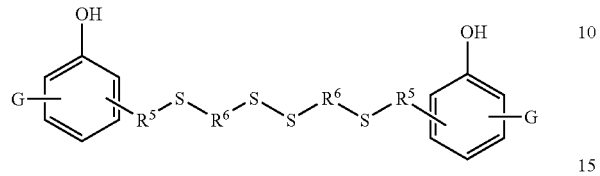

wherein $R^5$ may be the same or different from each other, and each represent an alkylene group having 2 or 3 carbon atoms, $R^6$ may be the same or different from each other, and each represent an alkylene group having 1 to 10 carbon atoms, G represents a hydrogen atom, an alkyl group having 1 to 10 carbon atoms, an alkoxyl group having 1 to 10 carbon atoms, a thioalkoxyl group having 1 to 10 carbon atoms, a hydroxyl group, a thiol group, a carboxyl group, a sulfonyl group, a nitro group, an amino group, a cyano group, a phenyl group, a benzyl group or a halogen atom.

* * * * *